US010555930B2

(12) United States Patent
Tang et al.

(10) Patent No.: US 10,555,930 B2
(45) Date of Patent: Feb. 11, 2020

(54) COMPLEX OF A GLUCOPYRANOSYL DERIVATIVE AND PREPARATION METHOD AND USE THEREOF

(71) Applicant: SUNSHINE LAKE PHARMA CO., LTD., Dongguan, Guangdong (CN)

(72) Inventors: Pengcho Tang, Dongguan (CN); Zheng Gu, Dongguan (CN); Wuyong Wu, Dongguan (CN); Zongyuan Zhang, Dongguan (CN); Panpan Kang, Dongguan (CN); Tong Qu, Dongguan (CN)

(73) Assignee: NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 0 days.

(21) Appl. No.: 15/778,220

(22) PCT Filed: Nov. 28, 2016

(86) PCT No.: PCT/CN2016/107543
§ 371 (c)(1),
(2) Date: May 22, 2018

(87) PCT Pub. No.: WO2017/088839
PCT Pub. Date: Jun. 1, 2017

(65) Prior Publication Data
US 2018/0344689 A1 Dec. 6, 2018

(30) Foreign Application Priority Data
Nov. 27, 2015 (CN) .......................... 2015 1 0851466

(51) Int. Cl.
| | | |
|---|---|---|
| *A61K 31/357* | (2006.01) | |
| *A61K 45/06* | (2006.01) | |
| *A61K 31/401* | (2006.01) | |
| *A61K 31/7048* | (2006.01) | |
| *C07D 493/08* | (2006.01) | |
| *C07D 207/28* | (2006.01) | |
| *C07H 7/04* | (2006.01) | |
| *A61P 5/48* | (2006.01) | |
| *A61P 9/10* | (2006.01) | |
| *A61P 13/12* | (2006.01) | |
| *C07H 1/00* | (2006.01) | |

(52) U.S. Cl.
CPC .......... *A61K 31/357* (2013.01); *A61K 31/401* (2013.01); *A61K 31/7048* (2013.01); *A61K 45/06* (2013.01); *A61P 5/48* (2018.01); *A61P 9/10* (2018.01); *A61P 13/12* (2018.01); *C07D 207/28* (2013.01); *C07D 493/08* (2013.01); *C07H 1/00* (2013.01); *C07H 7/04* (2013.01); *A61K 2300/00* (2013.01)

(58) Field of Classification Search
CPC .............. A61K 31/357; A61K 31/7048; A61K 31/401; A61K 45/06; C07H 7/04; C07H 1/00; C07H 9/04; A61P 13/12; A61P 9/10; A61P 5/48; C07B 2200/13
See application file for complete search history.

(56) References Cited

U.S. PATENT DOCUMENTS

| | | | |
|---|---|---|---|
| 9,394,329 B2 | 7/2016 | Wei et al. | |
| 2008/0004336 A1* | 1/2008 | Gougoutas | ............... C07H 7/04 514/460 |

FOREIGN PATENT DOCUMENTS

| | | |
|---|---|---|
| WO | 2015027963 | 3/2015 |
| WO | 2016173425 | 11/2016 |

OTHER PUBLICATIONS

Google Patents English language machine translation of WO 2015/027963, https://patents.google.com/patent/WO2015027963A1/en?oq=2015027963, accessed online on Jul. 5, 2019. (Year: 2019).*
Definition of prevent, Oxford English Dictionary Online, http://dictionary.oed.com/, accessed online Mar. 27, 2010, especially definition 9a. at p. 2. (Year: 2010).*
Entry for diabetes, Mayo Clinic, https://www.mayoclinic.org/diseases-conditions/diabetes, published Jul. 31, 2014, accessed online Oct. 17, 2019. (Year: 2014).*
ISR of PCT/CN2016/107543.
Written Opinion of the ISA of PCT/CN2016/107543.

* cited by examiner

*Primary Examiner* — Jonathan S Lau
(74) *Attorney, Agent, or Firm* — Kam Wah Law

(57) ABSTRACT

This present invention relates to a complex of a glucopyranosyl derivative and L-pyroglutamic acid as a sodium dependent glucose cotransporter (SGLT) inhibitor, and preparation processes thereof, and a pharmaceutical composition containing the complex, and their uses in the manufacture of a medicament for treating diabetes and/or diabetes-related diseases.

17 Claims, 5 Drawing Sheets

COMPLEX OF A GLUCOPYRANOSYL DERIVATIVE AND PREPARATION METHOD AND USE THEREOF

CROSS-REFERENCE TO RELATED APPLICATIONS

This is a U.S. national stage application of the International Patent Application No. PCT/CN2016/107543, filed Nov. 28, 2016, which claims priorities to Chinese Patent Application No. 201510851466.7, filed Nov. 27, 2015, both of which are incorporated herein by reference in their entirety.

FIELD OF THE INVENTION

The present invention relates to a complex of a glucopyranosyl derivative and L-pyroglutamic acid, a crystalline form and preparation methods thereof, and a pharmaceutical composition containing the complex of the invention, and use in the manufacture of a medicament as a sodium-dependent glucose transporter inhibitor.

BACKGROUND OF THE INVENTION

Diabetes mellitus is a common chronic disease, characterized by hyperglycemia. The onset of diabetes associates with insulin resistance in peripheral tissue, reduction of insulin in vivo and increase of gluconeogenesis in liver. When the disease cannot be controlled effectively through diet and exercise, insulin or oral hypoglycemic drugs for treatment are needed. At present, hypoglycemic drugs comprise biguanides, sulfonylureas, insulin sensitizers, glinides, α-glucosidase inhibitors and DPP-IV inhibitors, etc. However, these current hypoglycemic drugs have shortcomings. Biguanides can cause lactic acidosis. Sulfonylureas can result in severe hypoglycemia. Glinides can result in hypoglycemia if used improperly. Insulin sensitizers can lead to edema, heart failure and weight gain. α-Glucosidase inhibitors can cause abdominal bloating and diarrhea. DPP-IV inhibitors need to combine with metformin to achieve the desired effect of hypoglycemia. Therefore, there is an urgent need to develop novel, safer, and more effective hypoglycemic agents.

It has been found by research that glucose transporter proteins are a class of carrier proteins embedded in the cell membrane for transporting glucose. Glucose must be in virtue of glucose transporter protein to cross lipid bi-layer structure of cell membranes. Glucose transporter proteins are divided into two categories. The first category includes sodium-dependent glucose transporters (SGLTs), and the other category includes glucose transporters (GLUTs). Two major family members of SGLTs are SGLT-1 and SGLT-2. SGLT-1 is mainly distributed in small intestine, kidney, heart and windpipe, predominantly expressed in the intestinal brush border and the distal S3 segment of the renal proximal tubule, and a few expressed in heart and windpipe, and transports glucose and galactose with a sodium to glucose ratio of 2:1. While SGLT-2 is mainly distributed in kidney, predominantly expressed in the distal S1 segment of the renal proximal tubule, and transports glucose with a sodium to glucose ratio of 1:1. In biological bodies, glucose is transported by SGLTs through active transport against a concentration gradient with simultaneous energy consumption. While glucose is transported by GLUTs through facilitated diffusion along a concentration gradient without energy consumption in the transport process. Research indicates that normally plasma glucose is filtered in the kidney glomeruli in which 90% of glucose in the early S1 segment of the renal tubule is actively transported to epithelial cells by SGLT-2 and 10% of glucose in the distal S3 segment of the renal tubule is actively transported to epithelial cells by SGLT-1, and then transported to peripheral capillary network by GLUT of epithelial basement membrane accomplishing reabsorption of glucose by renal tubules. Hence, SGLTs is the first stage in regulation of glucose metabolism in cells, and an ideal target for treating diabetes effectively. It has been found by research that the patients with SGLT-2 impairment would excrete large amounts of urine glucose. This provides the factual basis of treating diabetes by reducing glucose uptake through inhibiting SGLT-2 activity. Therefore, inhibiting activity of SGLTs transport protein could block reabsorption of glucose in renal tubules and increase excretion of glucose in urine to normalize the plasma glucose concentration and further control the diabetes and diabetic complications. Inhibiting SGLTs would not influence the normal anti-regulatory mechanism of glucose, which may cause the risk of hypoglycemia. Meanwhile, lowering blood glucose through an increase of renal glucose excretion could promote weight loss in obese patients. It has also been found by research that the mechanism of action of SGLTs inhibitors is independent of pancreatic β cell dysfunction or the degree of insulin resistance. Therefore, the efficacy of SGLTs inhibitors will not decrease with the severe insulin resistance or β-cell failure. SGLTs inhibitors could be used alone or in combination with other hypoglycemic agents. Therefore, SGLTs inhibitors are ideal and novel hypoglycemic agents.

In addition, it has also been found by research that SGLTs inhibitors can be used for treating diabetes-related complications. Such as retinopathy, neuropathy, kidney disease, insulin resistance caused by glucose metabolic disorder, hyperinsulinemia, hyperlipidemia, obesity, and so on. Meanwhile, SGLTs inhibitors also be used in combination with current treatment regimens, such as sulphonamides, thiazolidinedione, metformin, and insulin, etc., which can reduce the dose without impacting on the effectiveness of the medicine, and thereby avoid or reduce side effects, and improve patient compliance. At present, the marketed SGLTs inhibitors comprise Canagliflozin and Dapagliflozin, etc., which are mainly used for treating diabetes type II and diabetes complications.

Chemical stability, solid state stability and "storage duration" of an active compound are particularly important factors in a drug preparation. For example, the compound is generally milled to a suitable size in order to ensure an even distribution of the active compound in a preparation process. In order to avoiding a decomposition of the active compound in the milling process, a high stability of the active compound is very important. Ideal drug substances and a composition thereof can be stored effectively during the evaluation period, and there are no obvious changes in physical and chemical properties (e.g., chemical composition, density, water absorbing rate, solubility and dissolution rate, etc.) of the active constituent. A known amorphous form drug substance cannot solve the above problems well. For instance, a drug substance in an amorphous form is difficult to be managed and prepared, its solubility is unreliable and the chemical and physical property of which is usually unstable.

The application of a drug complex shows a broad development prospect in the field of medical science, a crystalline form of a complex, also known as a cocrystal form, is gradually become a new selection for a solid form of the active compound in a drug preparation, the potential solid form of the compound is broadened, the formation of a cocrystal form can provide a better way to change the physical and chemical properties of an active ingredient, the specific expected properties are realized by forming a cocrystal form of an active ingredient and a cocrystallization agent (ligand). The exploration of a complex of the medicinal compound and a cocrystal form thereof provides more opportunities to improve the overall performance of the pharmaceutical product.

SUMMARY OF THE INVENTION

This application is based on the discovery of the following questions and facts:

The applicant in the previous research work found that compound "(1R,2S,3S,4R,5S)-5-(4-chloro-3-(4-ethoxybenzyl)phenyl)-1-(1-hydroxyethyl)-6,8-dioxabicyclo[3.2.1]octane-2,3,4-triol" has an obvious inhibitory activity on SGLTs, the structure is shown below:

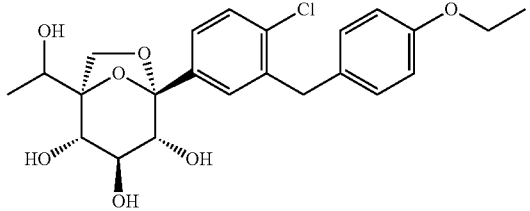

In a further research, the applicant of the present application prepared a singer (R)-isomer, i.e. (1R,2S,3S,4R,5S)-5-(4-chloro-3-(4-ethoxybenzyl)phenyl)-1-(1-(1R)-hydroxyethyl)-6,8-dioxabicyclo[3.2.1]octane-2,3,4-triol, by a stereoselectivity synthetic method, the applicant found that some properties about pharmacodynamics activity of the compound are obviously better than the (S)-isomer and the (R,S)-diastereomer mixture thereof.

Furthermore, the applicant found that the form of the compound prepared by the known synthetic method is an amorphous form, the stability of which can not satisfy the demand for the storage and preparation, therefore the inventors of the present application have studied the solid forms of the active compound. After a lot of screening experiments, it is surprised to find that a complex formed by the above active compound and L-pyroglutamic acid has an improvement crystalline property, compared to other complexes, which crystallizes more easily, and the crystalline form of the complex has very good stability and metabolic properties in vivo, and which is very suitable for preparing various drug formulations.

The present application specifically relates to a complex having Formula (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid, and a crystalline form thereof, i.e. a cocrystal form. The cocrystal form prepared herein can be identified by X-Ray single crystal diffraction, X-Ray powder diffraction (XRPD), differential scanning calorimetry (DSC), Raman spectrum and Fourier transform infrared (FT-IR) spectrum, and so on, and distinguished with other crystalline forms. The present invention also relates to a preparation method of the complex having Formula (IA), the method is easy for operation, and has good repeatability, and is controlled easily in the preparation process, the method is stability and has a high yield, which is suitable for industrial production. A property study of the complex having Formula (IA) found that the complex having Formula (IA) has obvious inhibition to SGLTs, and the complex has an appropriate solubility, especially has a significantly improvement stability and obviously decreased hygroscopicity. In addition, the complex having Formula (IA) also has a satisfactory pharmacokinetic feature in vivo, a good oral absorption, a high bioavailability, a long half-life, a lasting effect, and a good development prospect.

Based on a lot of experiments, in one aspect, the present invention provides a complex having Formula (IA),

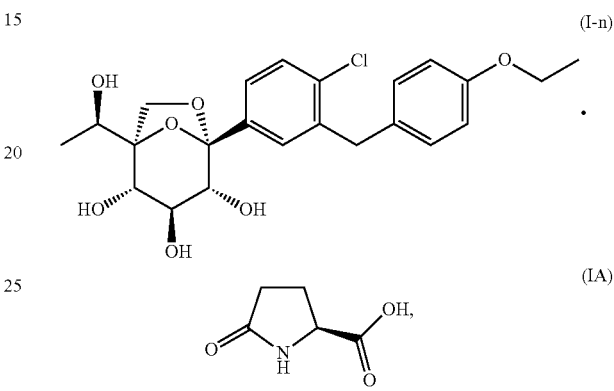

wherein the complex comprises compound having Formula (I-n) and L-pyroglutamic acid at a mole ratio of 1:1, compound having Formula (I-n) is (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol and its structure is shown below:

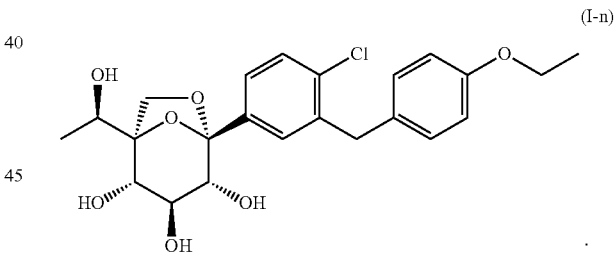

The complex having Formula (IA) described herein has obvious inhibition to SGLTs, and has an appropriate solubility, a significantly improvement stability, decreased hygroscopicity, pyro glutamic a satisfactory pharmacokinetic feature in vivo, a good oral absorption, a high bioavailability, a long half-life, a lasting effect and a good development prospect.

In some embodiments, the complex disclosed herein is a hydrate.

In some embodiments, the complex disclosed herein is a hydrate containing 1.25 equivalents of water of crystallization, i.e. Compound having Formula (I-n), L-pyroglutamic acid and water are at a mole ratio of 1:1:1.25.

In some embodiments, the complex disclosed herein is in a solid form; In other some embodiments, the complex disclosed herein is in a crystalline form.

In some embodiments, the complex disclosed herein has an X-ray powder diffraction pattern comprising peaks at scattering angles (2θ) of 3.61°±0.2°, 13.35°±0.2°, 17.84°±0.2°, 18.22°±0.2°, 19.92°±0.2° and 21.43°±0.2°.

In some embodiments, the complex disclosed herein has an X-ray powder diffraction pattern comprising peaks at scattering angles (2θ) of 3.61°±0.2°, 7.14°±0.2°, 13.35°±0.2°, 17.84°±0.2°, 18.22°±0.2°, 19.92°±0.2°, 21.43°±0.2° and 22.70°±0.2°.

In some embodiments, the complex disclosed herein has an X-ray powder diffraction pattern comprising peaks at scattering angles (2θ) of 3.61°±0.2°, 7.14°±0.2°, 11.44°±0.2°, 11.84°±0.2°, 13.35°±0.2°, 16.33°±0.2°, 16.71°±0.2°, 17.16°±0.2°, 17.84°±0.2°, 18.22°±0.2°, 19.92°±0.2°, 21.43°±0.2°, 22.70°±0.2° and 22.96°±0.2°.

In some embodiments, the complex disclosed herein has an X-ray powder diffraction pattern comprising peaks at scattering angles (2θ) of 3.61°±0.2°, 7.14°±0.2°, 11.44°±0.2°, 11.84°±0.2°, 13.35°±0.2°, 16.33°±0.2°, 16.71°±0.2°, 17.16°±0.2°, 17.84°±0.2°, 18.22°±0.2°, 18.52°±0.2°, 19.92°±0.2°, 21.43°±0.2°, 21.74°±0.2°, 22.70°±0.2°, 22.96°±0.2°, 23.75°±0.2°, 24.31°±0.2°, 25.07°±0.2°, 25.84°±0.2°, 26.50°±0.2°, 27.75°±0.2°, 28.61°±0.2°, 29.25°±0.2°, 29.44°±0.2°, 30.17°±0.2°, 30.99°±0.2°, 31.59°±0.2°, 32.40°±0.2°, 32.81°±0.2°, 34.32°±0.2°, 34.79°±0.2°, 35.43°±0.2°, 36.09°±0.2° and 38.03°±0.2°.

In some embodiments, the complex disclosed herein has an X-ray powder diffraction (XRPD) pattern substantially the same as shown in FIG. 2.

In some embodiments, the complex disclosed herein has a differential scanning calorimetry (DSC) thermogram comprising an endothermic peak at 96.9° C.±3° C.

In other some embodiments, the complex disclosed herein has a differential scanning calorimetry (DSC) thermogram comprising an endothermic peak at 96.9° C.±4° C.

In other some embodiments, the complex disclosed herein has a differential scanning calorimetry (DSC) thermogram comprising an endothermic peak at 96.9° C.±5° C.

In some embodiments, the complex disclosed herein has a Raman spectrogram comprising absorption peaks at 1454.51 $cm^{-1}$±1 $cm^{-1}$, 1303.40 $cm^{-1}$±1 $cm^{-1}$, 1183.17 $cm^{-1}$±1 $cm^{-1}$, 1012.34 $cm^{-1}$±1 $cm^{-1}$ and 495.61 $cm^{-1}$±1 $cm^{-1}$.

In some embodiments, the complex disclosed herein has an infrared spectrogram comprising absorption peaks at 3259.22 $cm^{-1}$±5 $cm^{-1}$, 2985.55 $cm^{-1}$±5 $cm^{-1}$, 2926.65 $cm^{-1}$±5 $cm^{-1}$, 1750.08 $cm^{-1}$±2 $cm^{-1}$, 1648.90 $cm^{-1}$±2 $cm^{-1}$, 1511.90 $cm^{-1}$±2 $cm^{-1}$, 1475.81 $cm^{-1}$±2 $cm^{-1}$, 1263.43 $cm^{-1}$±2 $cm^{-1}$, 1238.92 $cm^{-1}$±2 $cm^{-1}$, 1206.04 $cm^{-1}$±2 $cm^{-1}$, 1088.08 $cm^{-1}$±2 $cm^{-1}$, 1060.72 $cm^{-1}$±2 $cm^{-1}$, 1010.97 $cm^{-1}$±2 $cm^{-1}$ and 821.26 $cm^{-1}$+2 $cm^{-1}$.

In some embodiments, the complex disclosed herein has at least one of the following features:
(i) a differential scanning calorimetry thermogram substantially the same as shown in FIG. 3;
(ii) a Raman spectrogram substantially the same as shown in FIG. 4;
(iii) a Fourier transform infrared spectrogram substantially the same as shown in FIG. 5; and
(iv) the following unit cell parameters:
Unit Cell Dimension: a=7.4751 (2) Å, b=7.8333 (3) Å, c=49.4417 (19) Å, α=90°, β=90°, γ=90°;
Space Group: orthogonality, P $2_1$ $2_1$ $2_1$;
Cell Volume: 2895.04 Å$^3$; and
Number of asymmetric unit per unit cell (Z): 4.

In other aspect, the present invention relates to a process of preparing the complex disclosed herein, wherein the process comprises the steps of:

(i) dissolving compound having Formula (I-n) and L-pyroglutamic acid in a solvent;
(ii) cooling the solution obtained from step (i) to precipitate a solid; and
(iii) separating the solid obtained from step (ii).

The process of preparing the complex is easy for operation, and has good repeatability, and is controlled easily in the preparation process, the method is stability and has a high yield, which is suitable for industrial production. The prepared complex has obvious inhibition to SGLTs, and has an appropriate solubility, a significantly improvement stability, decreased hygroscopicity, a satisfactory pharmacokinetic feature in vivo, a good oral absorption, a high bioavailability, a long half-life, a lasting effect and a good development prospect.

In some embodiments, the solvent in step (i) is a mixture of alcohols and water; In some embodiments, the alcohols is ethanol or isopropanol; In some embodiments, the solvent is a mixture of ethanol and water at a volume ratio from (1:1) to (1:2) or a mixture of isopropanol and water at a volume ratio from (1:1) to (1:2); In other embodiments, the mixture is a mixture of ethanol and water at a volume ratio of (5:6).

In some embodiments, the amount of the solvent in step (i) is from 1.5 mL to 5 mL per gram of Compound (having Formula (I-n)); In other embodiments, the amount of the solvent in step (i) is from 2 mL to 3 mL per gram of Compound (having Formula (I-n)).

In some embodiments, the mole ratio of Compound (having Formula (I-n)) and L-pyroglutamic acid in step (i) is from (1:2) to (1:5); In some embodiments, the mole ratio of Compound (having Formula (I-n)) and L-pyroglutamic acid in step (i) is from (1:3) to (1:4).

In some embodiments, the dissolving temperature of Compound (having Formula (I-n)) and L-pyroglutamic acid in step (i) is from 50° C. to 90° C.; In some embodiments, the dissolving temperature is from 70° C. to 90° C.

In some embodiments, the cooling step (ii) is natural cooling at a temperature from 10° C. to 30° C.; In some embodiments, the cooling step (ii) is natural cooling at a temperature from 20° C. to 30° C.

In some embodiments, the dissolving step (i) is performed with stirring.

In some embodiments, the solid can precipitate in step (ii) under a stirring condition, also under a standing condition, the stirring can make the temperature of the solution uniformity in the vessel.

In some embodiments, the time of precipitation in step (ii) will be prolonged accordingly with the amount of Compound (having Formula (I-n)) increasing to ensure the solid precipitates completely.

In some embodiments, the separation method in step (iii) is filtration under vacuum suction, the solvent used for washing the solid after separation is a mixture of alcohols and water; In some embodiments, the solvent used for washing the solid after separation is a mixture of alcohols and water, the alcohols is ethanol or isopropanol; In some embodiments, the solvent used for washing the solid after separation is a mixture of ethanol and water at a volume ratio from (1:1) to (1:2) or a mixture of isopropanol and water at a volume ratio from (1:1) to (1:2); In other embodiments, the washing solvent is needed to precool to −20° C. to 0° C.; In another embodiments, the washing solvent is needed to precool to −20° C. to −10° C.

In some embodiments, the separated solid can be dried using a conventional drying method in the field, such as ambient pressure drying or hypobaric drying, the dry temperature can be 40° C. to 70° C.

In other aspect, the present invention relates to a process of preparing the complex disclosed herein, wherein the process comprises the steps of:

(i) dissolving compound (having Formula (I-n)) and L-pyroglutamic acid in a solvent;

(ii) cooling the solution obtained from step (i) to precipitate a solid; and (iii) separating the solid obtained from step (ii), wherein, in step (i), the solvent is a mixture of ethanol and water at a volume ratio (1:1) to (1:2) or a mixture of isopropanol and water at a volume ratio from (1:1) to (1:2);

the amount of the solvent is from 1.5 mL to 5 mL per gram of compound having Formula (I-n), the mole ratio of compound having Formula (I-n) and L-pyroglutamic acid is from (1:3) to (1:4), the dissolving temperature is from 70° C. to 90° C., in step (ii), the cooling is natural cooling at a temperature from 10° C. to 30° C., in step (iii), the separating is filtration under vacuum suction, wherein the filtration under vacuum suction further compromising washing the solid after separation, wherein the solid after separation is washed with a mixture of ethanol and water at a volume ratio from (1:1) to (1:2) or a mixture of isopropanol and water at a volume ratio from (1:1) to (1:2), wherein the mixture is precooled to −20° C.~0° C.

The process of preparing the complex is easy for operation, and has good repeatability, and is controlled easily in the preparation process, the method is stability and has a high yield, which is suitable for industrial production. The prepared complex has obvious inhibition to SGLTs, and has an appropriate solubility, a significantly improvement stability, decreased hygroscopicity, a satisfactory pharmacokinetic feature in vivo, a good oral absorption, a high bioavailability, a long half-life, a lasting effect and a good development prospect.

In other aspect, provided herein is a pharmaceutical composition comprising the complex disclosed herein.

In some embodiments, the pharmaceutical composition further comprises a pharmaceutically acceptable adjuvant.

In some embodiments, the pharmaceutical composition further comprises an additional therapeutic agent, wherein the additional therapeutic agent is an anti-diabetic agent other than an SGLT-2 inhibitor, an antihyperglycemic agent, an antiadipositas drug, an antihypertensive agent, an antiplatelet agent, an antiatherosclerotic drug, a lipid-lowering agent, an anti-inflammatory or a combination thereof.

In some embodiments, the anti-diabetic agent other than an SGLT-2 inhibitor or antihyperglycemic agent is a biguanide, a sulfonylurea, a glucosidase inhibitor, a PPAR agonist (peroxisome proliferator-activated receptor agonist), an αP2 inhibitor (adipocyte fatty acid binding protein inhibitor), a PPARα/γ dual agonist (peroxisome proliferator-activated receptor α/γ dual agonist), a dipeptidyl peptidase IV (DPP-IV) inhibitor, a meglitinide, insulin, a glucagon-like peptide-1(GLP-1) inhibitor, a PTP1B inhibitor (protein tyrosine phosphatase 1B inhibitor), a glycogen phosphorylase inhibitor, a glucose-6-phosphatase inhibitor or a combination thereof.

In some embodiments, the lipid-lowering agent is an MTP inhibitor (microsomal triglyceride transfer protein inhibitor), an HMG-CoA reductase inhibitor (hydroxymethylglutaryl-CoA reductase inhibitor), a squalene synthase inhibitor, a fibrates lipid-lowering drug, an ACAT inhibitor (acyl cholesterol acyl transferase inhibitor), a lipoxygenase inhibitor, a cholesterol absorption inhibitor, an ileal Na(+)/bile acid cotransporter inhibitor, an upregulator of LDL receptor activity (an upregulator of low density lipoprotein receptor activity), a niacins lipid-lowering drug, a bile acid sequestrant or a combination thereof.

In other some embodiments, the lipid-lowering agent is pravastatin, simvastatin, atorvastatin, fluvastatin, cerivastatin, atavastatin, rosuvastatin or a combination thereof.

In other aspect, provided herein is use of the complex or the pharmaceutical composition disclosed herein in the manufacture a medicament for inhibiting SGLT-2.

In other aspect, provided herein is use of the complex or the pharmaceutical composition disclosed herein in the manufacture a medicament for inhibiting SGLT-1.

In other aspect, provided herein is use of the complex or the pharmaceutical composition disclosed herein in the manufacture a medicament for increasing the high density lipoprotein (HDL) level.

The present invention also provides use of the complex or the pharmaceutical composition thereof disclosed herein in the manufacture of a medicament for preventing or treating a disease, lessening a disease symptoms, delaying the progression or onset of a disease, wherein the disease is diabetes, a diabetic complication such as diabetic retinopathy, diabetic neuropathy, diabetic nephropathy; insulin resistance; hyperglycemia; hyperinsulinemia; elevated blood levels of fatty acids or glycerol; hyperlipidemia, such as hypertriglyceridemia; obesity; syndrome X; atherosclerosis or hypertension.

In other aspect, provided herein is the complex or the pharmaceutical composition disclosed herein for use in inhibiting SGLT-2.

In other aspect, provided herein is the complex or the pharmaceutical composition disclosed herein for use in inhibiting SGLT-1.

In other aspect, provided herein is the complex or the pharmaceutical composition disclosed herein for use in increasing the high density lipoprotein (HDL) level.

The present invention also provides the complex or the pharmaceutical composition thereof disclosed herein for use in preventing or treating a disease, lessening a disease symptoms, delaying the progression or onset of a disease, wherein the disease is diabetes, a diabetic complication such as diabetic retinopathy, diabetic neuropathy, diabetic nephropathy; insulin resistance; hyperglycemia; hyperinsulinemia; elevated blood levels of fatty acids or glycerol; hyperlipidemia, such as hypertriglyceridemia; obesity; syndrome X; atherosclerosis or hypertension.

In other aspect, provided herein is a method of inhibiting SGLT-2 in a patient comprising administering a therapeutically effective amount of the complex or the pharmaceutical composition disclosed herein to the patient.

In other aspect, provided herein is a method of inhibiting SGLT-1 in a patient comprising administering a therapeutically effective amount of the complex or the pharmaceutical composition disclosed herein to the patient.

In other aspect, provided herein is a method of increasing the high density lipoprotein (HDL) level in a patient comprising administering a therapeutically effective amount of the complex or the pharmaceutical composition disclosed herein to the patient.

The present invention also provides a method of preventing or treating a disease, lessening a disease symptoms, delaying the progression or onset of a disease in a patient comprising administering a therapeutically effective amount of the complex or the pharmaceutical composition thereof disclosed herein to the patient, wherein the disease is diabetes, a diabetic complication such as diabetic retinopathy, diabetic neuropathy, diabetic nephropathy; insulin resistance; hyperglycemia; hyperinsulinemia; elevated blood levels of fatty acids or glycerol; hyperlipidemia, such as hypertriglyceridemia; obesity; syndrome X; atherosclerosis or hypertension.

The foregoing merely summarizes certain aspects disclosed herein and is not intended to be limiting in nature. These aspects and other aspects and embodiments are described more fully below.

DETAILED DESCRIPTION OF THE INVENTION

The present invention relates to Complex (having Formula (IA)) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (having Formula (I-n)) and L-pyroglutamic acid, and to a cocrystal form thereof, and to a preparation method of the complex, and to a pharmaceutical composition containing the complex, and to uses of the complex and a pharmaceutical composition thereof in the manufacture of a medicament.

Of particular note is that all similar substitutions and modifications to the skilled person are obvious, and they are deemed to be included in the present invention. In the present invention, Complex (IA) may contain solvent, in some cases, the solvent contained in the complex contributes to inner stability of a crystalline form of the complex, the common solvents comprise water, ethanol, methanol, isopropanol, acetone, and so on. As long as Complex (IA) containing a certain amount of water or other solvent has any feature of Complex (IA) disclosed herein, all should be considered included in the scope of the present invention.

The features and advantages of the invention may be more readily understood by those of ordinary skill in the art upon reading the following detailed description. It is to be appreciated that certain features of the invention that are, for clarity reasons, described in the context of separate embodiments, may also be combined to form a single embodiment. Conversely, various features of the invention that are, for brevity reasons, described in the context of a single embodiment, may also be combined so as to form sub-combinations thereof.

Definitions and General Terminology

Unless otherwise stated, the terms of the invention used in specification and claims have the definitions blow.

Reference will now be made in details to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

The term "comprise" is an open expression, it means comprising the contents disclosed herein, but don't exclude other contents.

The term "complex" as used herein refers to an aggregate formed by a series of molecules (e.g. complex organic compounds, inorganic compounds) and simple substance with a certain (physiological and chemical) functionality or obvious (physical and chemical) characteristics.

The term "solvate" as used herein, means having on a surface, in a lattice or on a surface and in a lattice, a solvent such as water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidinone, nitromethane, polyethylene glycol, propanol, 2-propanone, pyridine, tetrahydrofuran, toluene, xylene, mixtures thereof and the like. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

When Complex (IA) disclosed herein is in a crystalline form, solvents exist in the lattice as a part of the molecular.

The term "solvent," as used herein, means a substance, typically a liquid, that is capable of completely or partially dissolving another substance, typically a solid. Solvents for the practice of this invention include, but are not limited to, water, acetic acid, acetone, acetonitrile, 1-butanol, 2-butanol, 2-butanone, butyronitrile, tert-butanol, chlorobenzene, chloroform, cyclohexane, 1,2-dichloroethane, dichloromethane, bis(2-butoxyethyl)ether, diisopropylamine, diisopropyl ether, 1,2-dimethoxyethane, N,N-dimethylacetamide, N,N-dimethylformamide, dimethylsulfoxide, 1,4-dioxane, glycol dimethyl ether, ethanol, ethyl acetate, ethylene glycol, ethyl formate, formic acid, heptane, isobutanol, isopropyl acetate, isopropylamine, methanol, anisole, methyl acetate, 4-methyl-2-pentanone, 2-methyltetrahydrofuran, tert-butyl methyl ether, 2-pentanone, 3-pentanone, 1-pentanol, 1,2-propanediol, 2-propanol, 1-propanol, propionitrile, pyridine, tetrahydrofuran, tetrahydropyrane, toluene, triethylamine, xylene, mixtures thereof and the like.

The term "equivalent" or the abbreviation thereof "eq" refers to an equivalent amount of other needed material per 1 equivalent of the basic material in accordance with equivalent relation in chemical reaction.

"Cocrystal" is a specific crystal structure formed by an active ingredient(s) and a suitable cocrystal former(s) (also be called ligand) through molecular recognition, and through intermolecular forces, such as hydrogen bonding, halogen bond, π stacking interactions, and van der Waals forces without destruction of the chemical bonds of the active ingredient. There is a fixed stoichiometric ratio of each component of a cocrystal form. A cocrystal is a multicomponent crystal, which includes both binary cocrystal formed by two neutral solid and polybasic cocrystal formed by salt or solvate with neutral solid. A crystal form of an active ingredient can influence many physicochemical properties thereof, these properties would have a direct impact on processing and/or preparation of drugs and corresponding final formulations, such as, a cocrystal can improve solubility, hygroscopicity, stability of an active pharmaceutical ingredient and preparation thereof (e.g. pressing-ability, fluidity, filtrability), and also would influence stability, dissolution rate and bioavailability of drugs. Cocrystal can influence quality, safety and effect of drugs.

A crystal form may be referred to herein as being characterized by graphical data "as depicted in" a figure. These data include, e.g. X-ray powder diffraction pattern, Raman spectrum, Fourier transform infrared spectrum, DSC curve and Solid state NMR spectroscopy. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the figures herein with graphical data generated for an unknown crystal form and confirm whether the two sets of graphical data are characterizing the same crystal form.

"XRPD" refers to X-ray powder diffraction.

The term "amorphous" or "amorphous form" is intended to mean that the substance, component, or product in question is not substantially crystalline as determined, lacking a characteristic crystal shape or crystalline structure, for instance, by XRPD or where the substance, component, or product in question, for example is not birefringent when viewed using a polarized light microscope, or an X-ray powder diffraction pattern has no sharp peaks. In some embodiments, the sample containing an amorphous substance is substantially free of other amorphous forms and/or crystal forms.

The term "polymorphic" or "polymorphism", as used herein, is defined as the possibility of at least two different crystalline arrangements for the same chemical molecule.

The terms "crystalline form", "crystal form", "polymorph", "polymorphs", "crystalmodification", "crystalline modification" and "polymorphic form" are understood as synonyms. The solid forms of the compound or complex of the invention include, but are not limited to, single- and multiple-component crystals, and/or polymorphic form of compound, solvate, hydrate, clathrate, cocrystal, salt, solvate of salt, hydrate of salt.

Well known technology for detection, identification, classification and qualitation of polymorphic form are, for example, but not limited to, differential scanning calorimetry (DSC), thermogravimetric analysis (TGA), X-Ray power diffraction (XRPD), X-Ray single crystal diffraction, vibrational spectrum, solution calorimetry, solid-state nuclear magnetic resonance (SSNMR), Fourier transform infrared spectrum (FT-IR spectrum), Raman spectrum, hot stage optical microscopy, scanning electron microscopy (SEM), electron crystallography and quantitative analysis, particle size analysis (PSA), surface area analysis, solubility, and rate of dissolution. Polymorphism can be characterised as the ability of a particular compound to crystallise in different crystal modifications whilst maintaining the same chemical formula. Polymorphs of a given substance are chemically identical in containing the same atoms bonded to one another in the same way, but differ in their crystal modifications, which can affect one or more physical properties such as dissolution rate, melting point, bulk density, stability, flow properties, etc. Such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the figures herein with graphical data generated for an unknown crystal form and confirm whether the two sets of graphical data are characterizing the same crystal form or two different crystal forms.

Unless otherwise indicated, as used herein to refer to the spectra or data presented in graphical form (e.g., XRPD, IR, Raman and NMR spectra), the term "peak" refers to a peak or other special feature that one skilled in the art would recognize as not attributable to background noise. The term "significant peaks" refers to peaks at least the median size (e.g., height) of other peaks in the spectrum or data, or at least 1.5, 2, or 2.5 times the median size of other peaks in the spectrum or data.

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. For example, see The United States Pharmacopeia #23, National Formulary #18, 1843-1844 pages, 1995. In the present case, a peak position variability of ±0.2° in 2θ will take into account these potential variations without hindering the unequivocal identification of the indicated crystal form. Confirmation of a crystal form may be made based on any unique combination of distinguishing peaks (in units of ° 2θ), typically the more prominent peaks. Therefore, in some embodiments, the crystalline compounds disclosed herein characterized by XRPD pattern with some peak positions, have essentially the same characteristics as XRPD pattern provided in appended drawings of the present invention. According to the state of the instrument for the experiment, the error margin in 2θ of the characteristic peaks is ±0.2°. That is, the XRPD pattern may be identical to that of FIG. 2, or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. Similarly, a person skilled in the art is capable of determining if a given diffraction angle (expressed in ° 2θ) obtained from an XRPD pattern is at about the same position as a value presented herein. As used herein, the X-axis of X-ray powder diffraction (XRPD) pattern is 2θ in degrees.

Similarly, as is well known in the area of differential scanning calorimetry (DSC), relative peak height of DSC thermogram depends on many factors related to sample preparation and geometric shapes of the instrument, while peak position is relatively insensitive to experiment details. Therefore, in some embodiments, the crystalline compounds disclosed herein characterized by DSC thermogram with some peak positions, have essentially the same characteristics as DSC thermogram provided in appended drawings of the present invention. According to the state of the instrument for the experiment or the preparation of the sample, the error margin in the melting peaks is ±3°, ±4° or ±5°.

As is well known in the area of Raman spectrum, relative peak position and shape of Raman spectrum depends on the frequency of scattered light formed from the interaction between sample molecule and light. Therefore, in some embodiments, the crystalline compounds disclosed herein characterized by Raman spectrum with some peak positions and shapes, have essentially the same characteristics as Raman spectrum provided in appended drawings of the present invention. According to the state of the instrument for the experiment, the error margin of the absorption peaks is ±1 $cm^{-1}$.

As is well known in the area of Fourier transform infrared spectrum, relative peak position and shape of infrared spectrum depends on the transition of the energy level of the covalent bond of sample molecule. Therefore, in some embodiments, the crystalline compounds disclosed herein characterized by Fourier transform infrared spectrum with some peak positions, have essentially the same characteristics as Fourier transform infrared spectrum provided in appended drawings of the present invention. According to Chinese Pharmacopoeia, 2010, appendix IV C-Infrared spectrophotometry, and the state of the instrument for the experiment, the error margin of the absorption peaks at about 3000 $cm^{-1}$ is ±5 $cm^{-1}$, at about 1000 $cm^{-1}$ is ±2 $cm^{-1}$.

As used herein, an X-ray powder diffraction (XRPD) pattern, a differential scanning calorimetry (DSC) thermogram, Raman spectrum or Fourier transform infrared spectrum that is "substantially the same as shown" in a figure refers to an X-ray powder diffraction (XRPD) pattern, a differential scanning calorimetry (DSC) thermogram, Raman spectrum or Fourier transform infrared spectrum having at least 50%, at least 60%, at least 70%, at least 80%, at least 90%, at least 95%, or at least 99% of the peaks shown in the figure.

As used herein, the term "combination" refers to a crystalline form containing a tautomer thereof, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; a crystalline form containing one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or a crystalline form containing other crystalline forms, i.e., the other crystalline forms have less than 20%, less than 10%, less than 5%, less than 3%, less than 1%, less than 0.5%, less than 0.1%, or less than 0.01% of the crystalline form, based on the total volume or weight of the crystalline form and one or more other crystalline forms.

As used herein, the term "relative intensity" refers to the intensity of a peak with respect to the intensity of the strongest peak in the X-ray powder diffraction (XRPD) pattern which is regarded as 100%.

Whenever a number having a value N is disclosed, any number having the value N±0.01, N±0.02, N±0.03, N±0.05, N±0.07, N±0.08, N±0.1, N±0.15 N±0.2, N±1, N±1.5, N±2, N±3, N±4, N±5, N±6, N±7, N±8, N±9, or N±10 is specifically disclosed, wherein "±" refers to plus or minus. Whenever a numerical range with a lower limit, RL, and an upper limit, RU, is disclosed, any number falling within the range is specifically disclosed.

The crystalline form of the complex of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol and L-pyroglutamic acid provided herein exists in a substantially pure crystal morphology.

As used herein, the term "substantially pure" refers to chemical purity and crystal purity, more specifically, a crystalline form that is substantially free of one or more other crystalline forms, i.e., the crystalline form has a purity of at least about 50%, at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form contains one or more other crystalline forms, or the percentage of the crystalline form is less than 40%, less than 30%, less than 20%, less than 10%, less than 5%, less than 3%, less than 1%, less than 0.5%, less than 0.1%, or less than 0.01% in the total volume or weight of the crystalline form.

The purity of the crystal of the present invention can be determined by, for example, known methods such as X-ray powder diffractometry, thermal analysis, and the like. The purity of the crystal or mixed crystal of the present invention does not need to be 100%, and may be not less than 70%, preferably not less than 80%, more preferably not less than 90%, more preferably not less than 95%, more preferably not less than 98%. Purity within this range is preferable for guaranteeing the quality.

As used herein, "about" or "approximately" shall generally mean within 10 percent, preferably within 5 percent, and more preferably within 1 percent of a given value or range. Alternatively, the term "about" means within an acceptable standard error of the mean, when considered by one of ordinary skill in the art.

Unless stated otherwise, percentages stated throughout this specification are weight/weight (w/w) percentages.

The term "natural cooling" refers to the cooling way of heat taken away by the process of the circulation of the fluid which is produced by the change of density with temperature.

The term "alcohols solvent" refers to a liquid alcohol can be used as a solvent, wherein, a compound containing hydroxy connected with hydrocarbyl or carbon of side chain on a benzene ring is called alcohol. The alcohols include, but are not limited to, methanol, ethanol, propanol, i-propanol, n-butanol, i-butanol, phenylcarbinol or ethanediol.

The term "pharmaceutical composition" refers to a mixture of the commplex or cocrystal described herein, and other chemical components, such as physiologically/pharmaceutically acceptable carriers, excipients, diluents, fillers, or other excipients in common use, and other additional therapeutic agents, such as anti-diabetic agents, antihyperglycemic agents, antiadipositas agents, antihypertensive agents, antiplatelet agents, antiatherosclerotic agents, lipid-lowering agents, etc. The purpose of the pharmaceutical composition is to facilitate administration of a compound to an organism.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "syndrome X", also known as conditions, diseases of metabolic syndrome, the disorders are detailed in Johannsson et al., J. Clin. Endocrinol. Metab., 1997; 82, 727-734, which is incorporated herein by reference.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The Pharmaceutical Compositions of the Complex in the Invention

As described above, the pharmaceutically acceptable composition disclosed herein further comprise a pharmaceutically acceptable an adjuvant, such adjuvant, which, as used herein, includes any and all solvents, solid excipients, diluents, binders, disintegrants, or other liquid excipients, dispersion, corrigents or suspension aids, surface active agents, isotonic agents, thickening or emulsifying agents, preservatives, solid binders, glidants, lubricants and the like, as suited to the particular dosage form desired. As described in following references: In Remington: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various adjuvants used in formulating pharmaceutically acceptable compositions and known techniques for the preparation thereof. Except insofar as any conventional adjuvant incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable adjuvants include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The complex or a cocrystal or a pharmaceutical composition thereof disclosed herein can be administered as the sole active drug or in combination with one or more other additional therapeutic (pharmaceutical) agents where the combination causes no unacceptable adverse effects. This may be of particular relevance for the treatment of diabetes, diabetic complications and other related diseases. Some non-limiting examples of these diseases include diabetes mellitus type I, diabetes type II, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis and hypertension. As used herein, the additional therapeutic agents include an anti-diabetic agent other than an SGLT-2 inhibitor, an antihyperglycemic agent, an anti-adipositas drug, an antihypertensive agent, an antiplatelet agent, an antiatherosclerotic drug, a lipid-lowering agent, an anti-inflammatory or a combination thereof.

Wherein, the anti-diabetic agents other than an SGLT-2 inhibitor include, but are not limited to, a biguanide (e.g., phenformin and metformin), a sulfonylurea (e.g., acetohexamide, chlorpropamide, glibenclamide, glipizide, gliclazide, glimepiride, glipentide, gliquidone, tolazamide and tolbutamide), a meglitinide, a glinide (e.g., repaglinide, nateglinide), a glucosidase inhibitor (e.g., acarbose, adiposine, camiglibose, emiglitate, miglitol, voglibose, pradimicin and salbostatin), a PPAR agonist (e.g., balaglitazone, ciglitazone, darglitazone, englitazone, isaglitazone, pioglitazone, rosiglitazone and troglitazone), a PPARα/γ dual agonist (such as CLX-0940, GW-1536, GW-1929, GW-2433, KRP-297, L-796449, LR-90, MK-0767 and SB-219994), a DPP-IV inhibitor (e.g., sitagliptin, vidagliptin, alogliptin, linagliptin and saxagliptin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal extract and compounds are disclosed by Zhang, S.

et al., Drug Discovery Today, 12(9/10), 373-381, 2007), insulin, an insulin mimetic, a glycogen phosphorylase inhibitor, a VPAC2 receptor agonist, a glucokinase activator, a glycogen phosphorylase inhibitor or a glucose-6-phosphatase inhibitor, an $\alpha$P2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the antihyperglycemic agents include, but are not limited to, a biguanide (e.g., phenformin and metformin), a sulfonylurea (e.g., acetohexamide, chlorpropamide, glibenclamide, glipizide, gliclazide, glimepiride, glipentide, gliquidone, tolazamide and tolbutamide), a meglitinide, a glinide (e.g., repaglinide, nateglinide), a glucosidase inhibitor (e.g., acarbose, adiposine, camiglibose, emiglitate, miglitol, voglibose, pradimicin and salbostatin), a PPAR agonist (e.g., balaglitazone, ciglitazone, darglitazone, englitazone, isaglitazone, pioglitazone, rosiglitazone and troglitazone), a PPAR$\alpha$/$\gamma$ dual agonist (such as CLX-0940, GW-1536, GW-1929, GW-2433, KRP-297, L-796449, LR-90, MK-0767 and SB-219994), a DPP-IV inhibitor (e.g., sitagliptin, vidagliptin, alogliptin and saxagliptin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal extract and compounds are disclosed by Zhang, S. et al., Drug Discovery Today, 12(9/10), 373-381, 2007), insulin, an insulin mimetic, a glycogen phosphorylase inhibitor, a VPAC2 receptor agonist, a glucokinase activator, a glycogen phosphorylase inhibitor or a glucose-6-phosphatase inhibitor, an $\alpha$P2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the lipid-lowering agents include, but are not limited to, an MTP inhibitor, an HMG-CoA reductase inhibitor (hydroxymethylglutaryl-CoA reductase inhibitor), a squalene synthase inhibitor, a fibrate antihyperlipidemic drug, an ACAT inhibitor (acyl cholesterol acyl transferase inhibitor), a lipoxygenase inhibitor, a cholesterol absorption inhibitor, an ileal Na(+)/bile acid cotransporter inhibitor, an upregulators of LDL receptor activity, a bile acid sequestrant or niacins lipid-lowering drug. In some embodiments, the lipid-lowering agent is selected from pravastatin, simvastatin, atorvastatin, fluvastatin, cerivastatin, atavastatin and rosuvastatin. Wherein, the anti-obesity agents include CB-1 antagonists (such as rimonabant, taranabant, surinabant, otenabant, SLV319 and AVE1625), gut-selective MTP inhibitors (such as dirlotapide, mitratapide and implitapide), CCKa agonists, 5-HT2c agonists (such as lorcaserin), MCR4 agonists, lipase inhibitors (such as cetilistat), $PYY_{3-36}$, opioid antagonist (such as naltrexone), oleoyl-estrone, obinepitide, pramlintide, tesofensine, leptin, liraglutide, bromocriptine, orlistat, exenatide, ACM-9604 and sibutramide.

Wherein, the suitable anti-inflammatory agents include genital tract/urinary tract infection preventatives and treatments. Exemplary agents include cranberries (*Vaccinium macrocarpon*) and cranberry derivatives, such as cranberry juice, cranberry extracts or flavonols of cranberries. Moreover, other suitable anti-inflammatory agents include, but are not limited to, aspirin, non-steroidal anti-inflammatory drugs, glucocorticosteroid, sulfasalazine and selective cyclooxygenase-2 inhibitors, etc.

The compositions disclosed herein may be administered orally, parenterally, topically, buccally, or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection and infusion techniques. In some embodiments, the compositions are administered orally, intraperitoneally or intravenously. Sterile injectable forms of the compositions disclosed herein include aqueous and oleaginous suspension. These suspensions may be formulated according to techniques known in the art using suitable dispersing or wetting agents and suspending agents.

The pharmaceutically acceptable composition of the present invention can be an acceptable oral formulation for oral administration, including but not limited to, capsules, tablets, water suspension or solution. For oral tablets, carriers generally include lactose and corn starch. Lubricants such as magnesium stearate, are typically added. For oral capsule administration, suitable diluents include lactose and dried corn starch. When oral formulation is a water suspension, the active ingredients can be comprised of emulsifier and suspending agent. For these formulations, sweeteners, flavoring agents or colorants can be added.

Liquid formulations for oral administration include, but are not limited to, pharmaceutically acceptable emulsions, micro-emulsion, solution, suspension, syrup and elixir. In addition to the active compounds, the liquid dosage forms may contain inert diluents known in the art, for example, water or other solvent, solubilizer and emulsifier, such as ethanol, isopropanol, ethyl carbonate, ethyl acetate, benzyl alcohol, benzyl benzoate, propylene glycol, 1,3-butanediol, dimethylformamide, oils and fats (in particular, cottonseed, groundnut, corn, microbes, olive, castor and sesame oil), glycerin, 2-tetrahydrofuranmethanol, polyethyleneglycol, dehydrated sorbitol fatty acid esters, and their mixtures. Addition to inert diluents, the oral compositions can also contain adjuvants such as wetting agents, emulsifiers or suspending agent, sweeteners, flavorings and fragrances.

Injection, such as sterile injection or oily suspensions can be prepared by well known technology using suitable dispersing agents, wetting agents and suspending agent. Sterile injection can be prepared at the location of application by a non-toxic locally acceptable diluent or solvent to give sterile injection, suspension or emulsion, for example, 1,3-butanediol solution. Acceptable excipients and solvents are water, Ringer's solution, USP and isotonic sodium chloride solution. In addition, sterile, non-volatile oil has been used as the solvent or suspension medium. Any mild, non-volatile oil used for this purpose may include the synthetic mono or di-glucosyl diacylglycerol. In addition, fatty acids such as oleic acid can be used in injection, can be used as natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Sterilization methods of injection include, but are not limited to, such as filtration through a sterilization filter, or incorporation of a sterilizing agent in the form of sterile solid compositions. Sterilizing agent can be dissolved in or dispersed in sterile water or sterile injection medium prior to use. In order to prolong the effect of the compounds of the invention, subcutaneous or intramuscular injection can be used to slow the absorption of compounds. The problem of poor water solubility of the crystal or non-crystalline material can be solved by using liquid suspension. The absorption rate of the compound depends on its dissolution, in turn depends on grain size and crystal shape. In addition, the compound is dissolved or dispersed in the oil excipient to delay absorption of the compound injection.

Drug releasing forms of injectable in vivo are through forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly (orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or calcium phosphate and/or a) fillers or extenders such as starches, lactose, sucrose, glucose, mannitol, and silicic acid; b) binders such as carboxymethylcellulose, alginates, gelatin, povidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage form may also comprise buffering agents. They may optionally contain pacifying agents and can also be of a composition that they release the active ingredient(s) only, or in other embodiments, in a certain part of the intestinal tract, optionally, in a delayed manner. Some non-limiting examples of embedding compositions that can be used include polymeric substances and waxes.

The complexes disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Use of the Complexes and Pharmaceutical Compositions

The amount of the complex or the active Compound (I-n) in the compositions disclosed herein is an effective and detectable amount for inhibiting sodium-dependent glucose transporters (SGLTs) activity, including SGLT-1 and SGLT-2 activity, especially SGLT-2 activity. SGLT-2 is responsible for re-absorption of D-glucose from kidney spherule filtrate, which inhibits glucose re-absorption in blood vessel and this is beneficial to reduce glucose concentrations in blood. Hence, the complex and/or the pharmaceutical composition of the invention would be used for preventing and treating the type II diabetes and related diseases or improving symptoms of these diseases. Also, the amount of the complex or the active Compound (I-n) in the compositions disclosed herein is an effective and detectable amount for elevating the high density lipoprotein level.

The complex and a pharmaceutical composition thereof disclosed herein would be useful for, but are not limited to, preventing or treating diabetes or related diseases, or lessening diabetes or related diseases, or delaying the progression or onset of diabetes or related diseases or increasing the high density lipoprotein (HDL) levels in a patient by administering to the patient a complex and/or a pharmaceutical composition disclosed herein in an effective amount. Such diseases include, but are not limited to, diabetes, especially type II diabetes, and diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis and hypertension.

Moreover, the complex or a pharmaceutical composition thereof disclosed herein also suit for preventing or treating the damage of diabetes in later stages, such as kidney disease, retinopathy, neuropathy, myocardial infarction, peripheral arterial disease, thrombosis, arteriosclerosis, inflammation, immunological diseases, autoimmune diseases such as AIDS, asthma, osteoporosis, cancer, psoriasis, Alzheimer's disease, schizophrenia and infectious diseases.

Besides being useful for human treatment, these complexes are also useful for veterinary treatment of animals such as companion animals, exotic animals and farm animals, including mammals, rodents, and the like. In other embodiments, the animals disclosed herein include horses, dogs, and cats.

An "effective amount" or "effective dose" of the complex or pharmaceutically acceptable composition is an amount that is effective in treating or lessening the severity of one or more of the aforementioned disorders. The complexes and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The complexes and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A complex or composition can also be administered with one or more other therapeutic agents as discussed above.

GENERAL PREPARATION AND DETECTION METHODS

Figure 1:
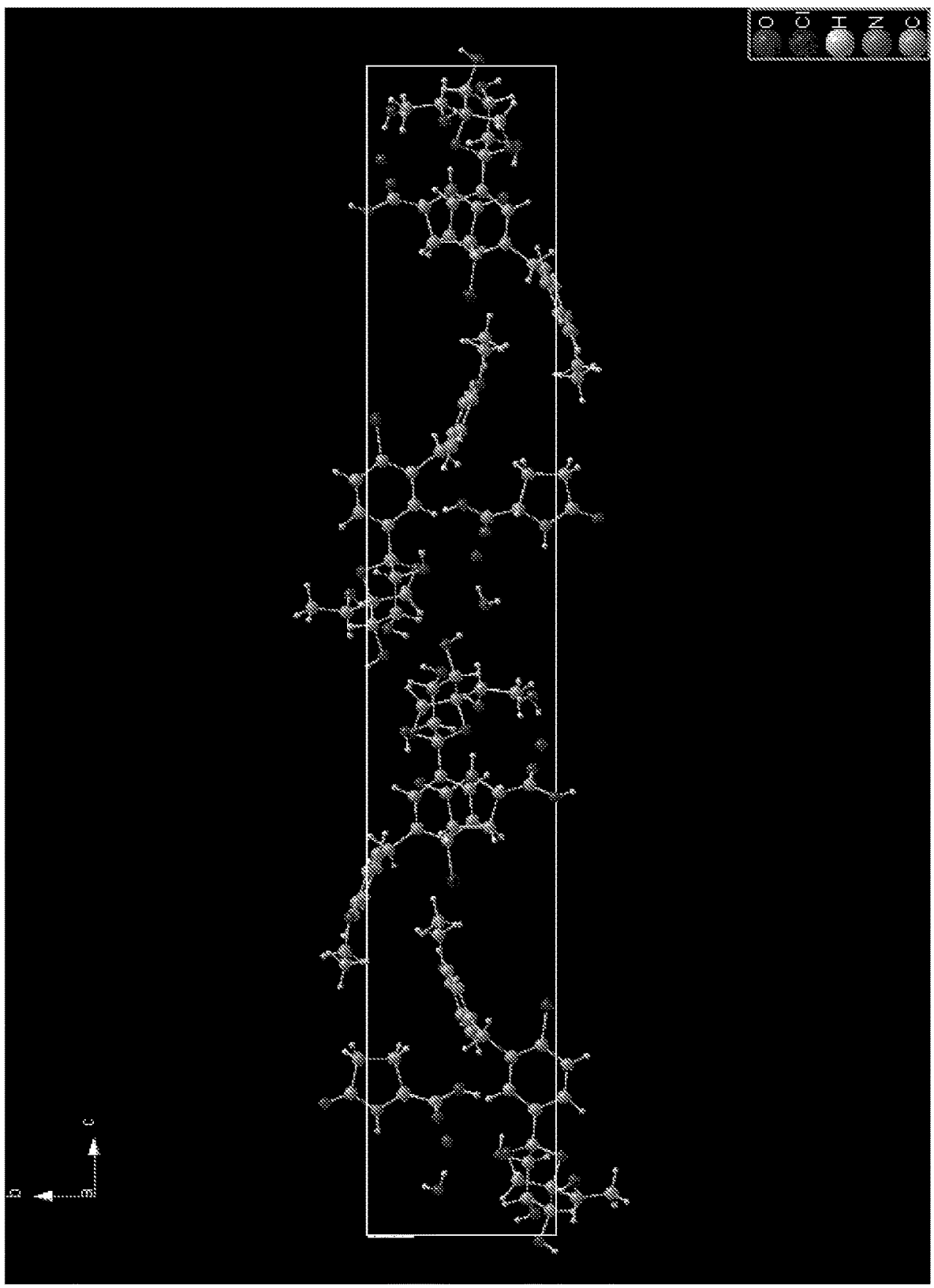
FIG. 1 is the unit cell figure of Complex (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid prepared herein.

The invention is illustrated further by the following examples, which are not be construed as a limitation of the scope of invention.

Skilled in the art can learn from this article to properly improve the experiment parameters to implement the preparation method. Of particular note is that all similar substitutions and modifications to the skilled person are obvious, and they are deemed to be included in scope of the present invention. Related person can clearly realize and apply the techniques disclosed herein by making some changes, appropriate alterations or combinations to the methods without departing from spirit, principles and scope of the present disclosure.

The structures of the compounds were identified by nuclear magnetic resonance (e.g., $^1$H-NMR and $^{13}$C-NMR). $^1$H-NMR and $^{13}$C-NMR chemical shifts ($\delta$) were recorded as ppm (10-6). Measure of $^1$H-NMR and $^{13}$C-NMR are performed, respectively, on Bruker Ultrashield—400 nuclear magnetic resonance spectrometer and Bruker Avance III HD 600 nuclear magnetic resonance spectrometer using deuterated chloroform (CDCl$_3$), deuterated methanol (CD$_3$OD) or deuterated DMSO (DMSO-d$_6$) as a solvent. TMS (0 ppm) or chloroform (7.25 ppm) is as the reference standard. When peak multiplicities were reported, the following abbreviations were used: s (singlet), d (doublet), t (triplet), m (multiplet), br (broadened), dd (doublet of doublets), and dt (doublet of triplets), coupling constant J is represented by Hz.

MS spectra were determined on Agilen-6120 Quadrupole LC/MS mass spectrometer;

The thin-layer silica gel used was Yantai Huanghai HSGF254 silica gel plate.

The silica gel used in column chromatography generally was Qingdao Ocean Chemical Factory 300 to 400 mesh silica gel.

The staring materials of the present invention were known or purchased from Shanghai Accela Company, Energy Company, J&K, Alfa Company and the like, or they could be prepared by the conventional synthesis methods in the prior art.

Unless otherwise stated, the reactions disclosed herein were carried out in a nitrogen atmosphere.

The term "nitrogen atmosphere" refers to such an atmosphere that a reaction flask was equipped with a balloon or a stainless steel autoclave filled with about 1 L nitrogen.

The term "hydrogen atmosphere" refers to such an atmosphere that a reaction flask was equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature, unless otherwise stated, the room temperature was from 20° C. to 30° C.

Unless otherwise stated, the reaction temperature or the drying temperature was the temperature shown on monitoring instrument, there was allowed to have ±5° C. error.

Crystalline forms may be prepared by a variety of methods including, but not limited to, for example, crystallization or recrystallization from a suitable solvent mixture; sublimation; solid state transformation from another phase; crystallization from a supercritical fluid; and jet spraying. Techniques for crystallization or recrystalhzation of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, 2nd Edition, SSCI, West Lafayette, Ind. (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the compound in the solution and precipitate the formation of crystals. An antisolvent is a solvent in which a compound has low solubility.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in Programmed Cooling Batch Crystallizers," J. W. Mullin and J. Nyvlt, Chemical Engineering Science, 1971, 26. 369-377. In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product is washed with a suitable solvent, such as, for example, cold recrystallization solvent. After being washed, the product may be dried under a nitrogen purge to afford the desired crystalline form. The product may be analyzed by a suitable spectroscopic or analytical technique including, but not limited to, for example, X-ray single crystal diffraction, X-ray powder diffraction (XRPD), differential scanning calorimetry (DSC), thermogravimetric analysis (TGA), Fourier transform infrared spectrum (FT-IR spectrum) and Raman spectrum, etc. To assure the crystalline form of the compound has been formed.

The invention is further illustrated by the following examples, the specific steps of the examples should not be understood as the limitation of scope of the disclosure.

In order to further understand the invention, it is detailed below through examples.

EXAMPLES

To be explained, in the following example, the complex which is required to be protected by the application is expressed in Complex (IA), and the other compounds are expressed as "the compound chemical name (structural code)", such as (R)-1-((1R,2S,3S,4R,5S)-2,3,4-tris(benzyloxy)-5-(4-chloro-3-(4-ethoxybenzyl)phenyl)-6,8-dioxabicyclo[3.2.1]octan-1-yl)ethanol (I-m).

1. Preparation Example

Preparation Example 1: (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n)

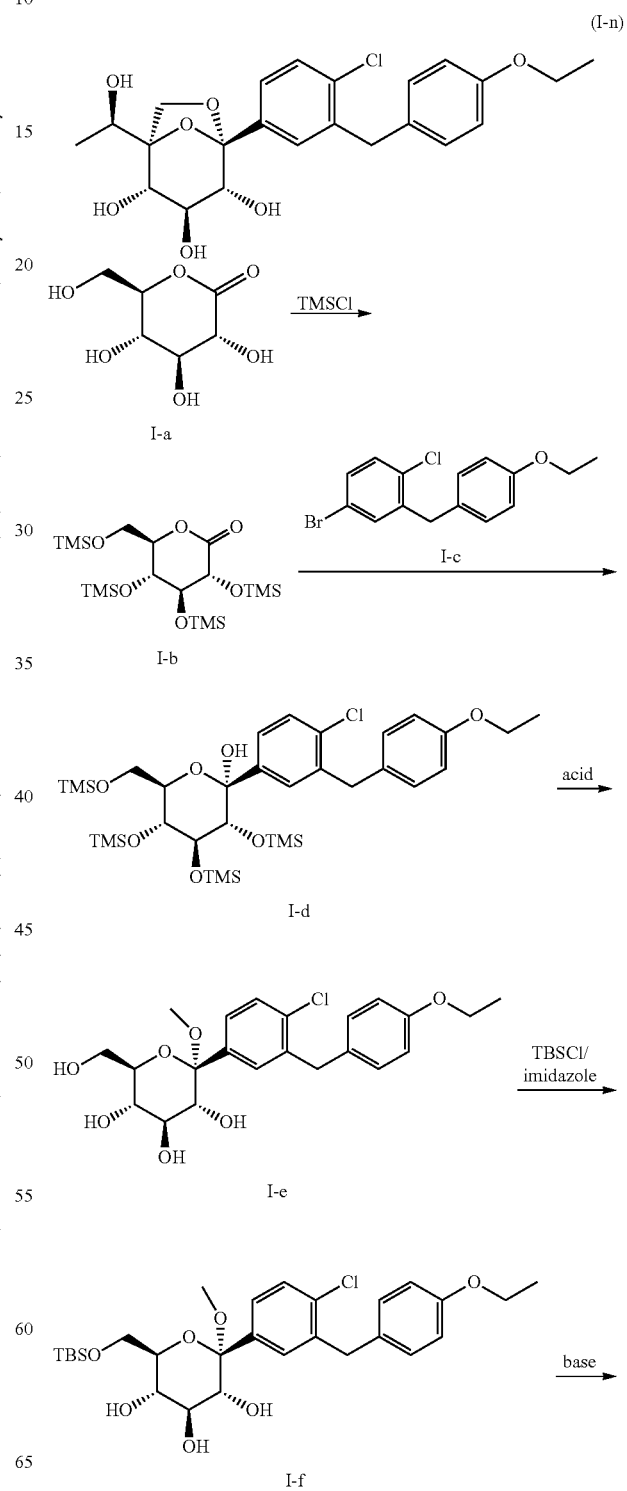

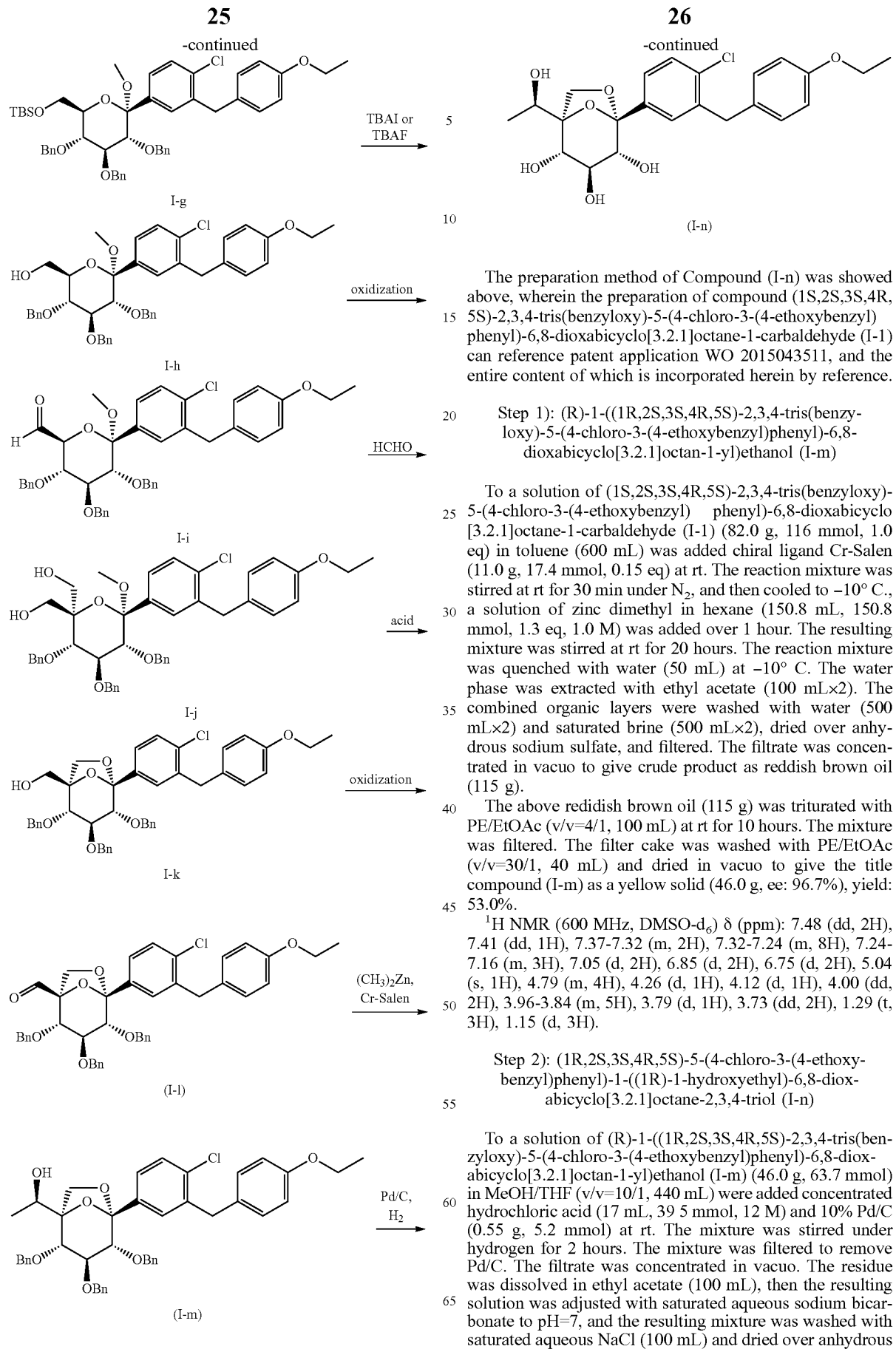

The preparation method of Compound (I-n) was showed above, wherein the preparation of compound (1S,2S,3S,4R,5S)-2,3,4-tris(benzyloxy)-5-(4-chloro-3-(4-ethoxybenzyl)phenyl)-6,8-dioxabicyclo[3.2.1]octane-1-carbaldehyde (I-1) can reference patent application WO 2015043511, and the entire content of which is incorporated herein by reference.

Step 1): (R)-1-((1R,2S,3S,4R,5S)-2,3,4-tris(benzyloxy)-5-(4-chloro-3-(4-ethoxybenzyl)phenyl)-6,8-dioxabicyclo[3.2.1]octan-1-yl)ethanol (I-m)

To a solution of (1S,2S,3S,4R,5S)-2,3,4-tris(benzyloxy)-5-(4-chloro-3-(4-ethoxybenzyl) phenyl)-6,8-dioxabicyclo[3.2.1]octane-1-carbaldehyde (I-1) (82.0 g, 116 mmol, 1.0 eq) in toluene (600 mL) was added chiral ligand Cr-Salen (11.0 g, 17.4 mmol, 0.15 eq) at rt. The reaction mixture was stirred at rt for 30 min under $N_2$, and then cooled to −10° C., a solution of zinc dimethyl in hexane (150.8 mL, 150.8 mmol, 1.3 eq, 1.0 M) was added over 1 hour. The resulting mixture was stirred at rt for 20 hours. The reaction mixture was quenched with water (50 mL) at −10° C. The water phase was extracted with ethyl acetate (100 mL×2). The combined organic layers were washed with water (500 mL×2) and saturated brine (500 mL×2), dried over anhydrous sodium sulfate, and filtered. The filtrate was concentrated in vacuo to give crude product as reddish brown oil (115 g).

The above redidish brown oil (115 g) was triturated with PE/EtOAc (v/v=4/1, 100 mL) at rt for 10 hours. The mixture was filtered. The filter cake was washed with PE/EtOAc (v/v=30/1, 40 mL) and dried in vacuo to give the title compound (I-m) as a yellow solid (46.0 g, ee: 96.7%), yield: 53.0%.

$^1$H NMR (600 MHz, DMSO-$d_6$) δ (ppm): 7.48 (dd, 2H), 7.41 (dd, 1H), 7.37-7.32 (m, 2H), 7.32-7.24 (m, 8H), 7.24-7.16 (m, 3H), 7.05 (d, 2H), 6.85 (d, 2H), 6.75 (d, 2H), 5.04 (s, 1H), 4.79 (m, 4H), 4.26 (d, 1H), 4.12 (d, 1H), 4.00 (dd, 2H), 3.96-3.84 (m, 5H), 3.79 (d, 1H), 3.73 (dd, 2H), 1.29 (t, 3H), 1.15 (d, 3H).

Step 2): (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n)

To a solution of (R)-1-((1R,2S,3S,4R,5S)-2,3,4-tris(benzyloxy)-5-(4-chloro-3-(4-ethoxybenzyl)phenyl)-6,8-dioxabicyclo[3.2.1]octan-1-yl)ethanol (I-m) (46.0 g, 63.7 mmol) in MeOH/THF (v/v=10/1, 440 mL) were added concentrated hydrochloric acid (17 mL, 39 5 mmol, 12 M) and 10% Pd/C (0.55 g, 5.2 mmol) at rt. The mixture was stirred under hydrogen for 2 hours. The mixture was filtered to remove Pd/C. The filtrate was concentrated in vacuo. The residue was dissolved in ethyl acetate (100 mL), then the resulting solution was adjusted with saturated aqueous sodium bicarbonate to pH=7, and the resulting mixture was washed with saturated aqueous NaCl (100 mL) and dried over anhydrous Na$_2$SO$_4$, and filtered. The filtrate was concentrated in vacuo to give crude product (I-n). To the crude product (I-n) (22.00 g, 48.84 mmol) was added anhydrous ethanol (88 mL). The resulting system was warmed to 80° C. and stirred until the crude product dissolved completely, and then cooled naturally to rt, the system was continued to stirred, and solid precipitated out. Until there was no solid precipitated out, the system was filtered by suction, the filter cake was collected and dried in vacuo to give Compound (I-n) as a white solid (18.70 g, 85%).

MS (ESI, pos. ion) m/z: 451.2 [M+H]+; and $^1$H NMR (600 MHz, DMSO-d$_6$) δ (ppm): 7.41 (dd, 2H), 7.35-7.29 (m, 1H), 7.11 (d, 2H), 6.84 (d, 2H), 5.30 (d, 1H), 5.01 (d, 1H), 4.92 (d, 1H), 4.64 (d, 1H), 4.03-3.95 (m, 5H), 3.85 (p, 1H), 3.78 (d, 1H), 3.59-3.53 (m, 1H), 3.44 (dd, 1H), 3.38 (m, 1H), 1.30 (t, 3H), 1.18 (d, 3H).

Preparation Example 2: Complex (IA) of (1R,2S,3S,4R,5S)-5-(4-chloro-3-(4-ethoxybenzyl) phenyl)-1-((1R)-1-hydroxyethyl)-6,8-dioxabicyclo[3.2.1]octane-2,3,4-triol (I-n) and L-pyroglutamic acid A mixture of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) (5.43 g, 10.8 mmol), L-pyroglutamic acid (5.60 g, 43.4 mmol), ethanol (5 mL) and water (6 mL) was heated to 80° C. and stirred for 1 h, the solid was dissolved completely to give a corlorless or yellowish transparent solution. The solution was stirred at rt until solid started to precipitate out, and the system was stood at rt for 12 h for crystallization. The mixture was filtered by suction, and the filter cake was washed with a mixed solvent of ethanol and water (v/v=2/3, 12 mL) precooled to −20° CThe filter cake was collected and dried at 50° C. in vacuo to constant weight (vacuum degree is −0.098 Mpa), to obtain . the product as a white cystal solid (5.50 g, 87%, HPLC: 99.6%).

Complex (IA) can be prepared under the reaction conditions shown in table 1 according to the procedure described in preparation example 2.

A variety of identification methods can confirm the formation of Complex (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid.

Preparation Example 3: The Single Crystal of Complex (IA)

The cocrystal sample (250 mg) prepared from example 2 was weighed into a vessel, and to which was added a mixed solvent of ethanol and water (0.25 mL/0.25 mL), then the mixture system was warmed to 50° C. and stirred until the solid dissolved completely, and further stirred for 0.5 h. The mixture was stopped to heated and then cooled to rt slowly, and a little of seed crystal (prepared from example 2) was added, then the resulting system was stood and tiny rods crystal precipitated out, i.e. the single crystal of Complex (IA).

2. Identification Example

Identification Example 1: Study of X-Ray Single Crystal Diffraction

Data were collected on an Agilent Technologies Gemini A Ultra serial diffractometer using Cu Kα radiation (λ=1.5418 Å). Indexing and processing of the measured intensity data were carried out with CrysAlis PRO procedure. The unit cell parameters were measured by pre-experiments, and the data collection was carried out by using data collection strategy designed according to the unit cell parameters.

The structure was solved by direct methods using SHELX-97 (Sheldrick, G. M. SHELXTL-97, Program for Crystal Structure Solution and Refinement; University of Gottingen: Gottingen, Germany, 1997). The derived atomic parameters (coordinates and temperature factors) were refined through full matrix least-squares. The function minimized in the refinements was $\Sigma_w (|F_o|-|F_c|)^2$. R is defined as

TABLE 1

The preparation conditions of Complex (IA)

| test number | material mass (g)/1.0 eq | solvent volume (mL) | solvent component | ligand L-pyroglutamic acid (g)/eq | Reaction time(h) | washing solvent in work-up (v/v) | yield (%) | purity (%) |
|---|---|---|---|---|---|---|---|---|
| 1 | 0.8 g | 2.0 mL | isopropanol/water, v/v = 1/1 | 0.41 g/2.0 eq | 1 | isopropanol/water v/v = 1/2 | 78 | 99.8 |
| 2 | 1.1 g | 3.0 mL | ethanol/water, v/v = 1/2 | 1.16 g/4.0 eq | 0.5 | ethanol/water v/v = 1/2 | 79 | 95.5 |
| 3 | 2.1 g | 5.0 mL | ethanol/water, v/v = 1/1 | 2.18 g/4.0 eq | 1 | ethanol/water v/v = 1/2 | 66.5 | 98.2 |
| 4 | 5.4 g | 11 mL | ethanol/water, v/v = 5/6 | 5.60 g/4.0 eq | 1 | ethanol/water v/v = 2/3 | 87 | 99.6 |
| 5 | 1.0 g | 2.2 mL | ethanol/water, v/v = 5/6 | 0.52 g/2.0 eq | 1 | ethanol/water v/v = 2/3 | 73 | 99.5 |
| 6 | 1.0 g$^j$ | 2.2 mL | ethanol/water, v/v = 5/6 | 0.78 g/3.0 eq | 1 | ethanol/water v/v = 2/3 | 79 | 99.6 |
| 7 | 1.0 g | 2.2 mL | ethanol/water, v/v = 5/6 | 1.30 g/5.0 eq | 1 | ethanol/water v/v = 2/3 | 82 | 99.6 |
| 8 | 1.0 g | 2.2 mL | ethanol/water, v/v = 1/1 | 1.04 g/4.0 eq | 1 | ethanol/water v/v = 2/3 | 79 | 99.7 |
| 9 | 1.0 g | 2.2 mL | ethanol/water, v/v = 2/3 | 1.04 g/4.0 eq | 1 | ethanol/water v/v = 2/3 | 86 | 98.5 |
| 10 | 1.0 g | 4.4 mL | ethanol/water, v/v = 2/3 | 1.04 g/4.0 eq | 1 | ethanol/water v/v = 2/3 | 72 | 99.6 |

Note:
eq is equivalent $\Sigma||F_o|-|F_c||/\Sigma|F_o|$, while $R_w=[\Sigma_w(|F_o|-|F_c|)^2/\Sigma_w|F_o|_2]^{1/2}$, where w is an appropriate weighting function based on errors in the observed intensities. Difference maps were examined at all stages of refinement. The positions of hydrogens on nitrogen were located in Fourier difference electron density maps. All the other hydrogen atoms were placed in calculated positions. Simulated powder X-ray patterns were generated using Mercury procedure.

Single crystal was selected by measuring 0.30×0.08×0.08 mm Single Crystal (prepared from example 3) by single crystal diffraction analysis. The selected crystal was affixed to a thin glass fiber with a small amount of Vaseline, and mounted on a Gemini A Ultra single crystal diffractometer (Agilent Technologies) and measured at about 150 K. Crystal cell parameters were listed in table 2 and atomic fractional coordinate was listed in table 3.

TABLE 2

| Crystal cell parameters |
|---|
| a = 7.4751 (2) Å |
| b = 7.8333 (3) Å |
| c = 49.4417 (19) Å |
| α = 90° |
| β = 90° |
| γ = 90° |
| Space Group: orthogonality, P $2_1 2_1 2_1$ |
| Z: 4 |
| Volume: 2895.04 Å$^3$ |

According to the research results of X-ray single crystal diffraction, unit cell of Complex (IA) contains 4 Compound (I-n) molecules, 4 L-pyroglutamic acid molecules and 5 water molecules, thus, the mole ratio of Compound (I-n), L-pyroglutamic acid and water may be confirmed as 1:1:1.25. Unit cell figure of crystal structure is shown as FIG. 1.

Identification Example 2: Analysis of X-Ray Powder Diffraction (XRPD)

An X-ray powder diffraction figure was recorded on Netherlands PANalytical Empyrean X-ray diffractometer equipped with transmission and reflection sample stage with an automated 3*15 zero background sample holder. The radiation source is (Cu, kα, Kα1 (Å): 1.540598; Kα2 (Å): 1.544426; Kα2/Kα1 intensity ratio: 0.50), wherein voltage is 45 KV, current is 40 mA. Divergence of X-ray beam, i.e. effective dimensions constrained by X-ray on sample, is 10 mm. An effective 2θ range of 3° to 40° is obtained by using a mode of θ-θ continuously scanning. An appropriate amount of powder sample was pressed gently using a clean glass slide in Circular groove of the zero background sample holder under an environment condition (about 18° C. to 32° C.) to get a flat plane, and the zero background sample holder was fixed. The test sample was and analyzed in the range from 3° to 40° with a 0.0167° step size to produce a traditional XRPD figure. Data were collected by Data Collector software, and processed by High Score Plus software, read by Data Viewer software.

TABLE 3

| Atomic fractional coordinate | | | | | | | |
|---|---|---|---|---|---|---|---|
| atom | X | Y | Z | atom | X | Y | Z |
| O1W | 0.1435(5) | 0.8744(6) | 0.96119(8) | H20 | 0.8109 | 0.1456 | 0.8829 |
| Cl1 | 0.94748(17) | 0.4540(2) | 0.80272(2) | H21 | 0.5581(5) | 0.6085(6) | 0.96735(8) |
| O2 | 0.7662(3) | 0.5271(3) | 0.93231(5) | C22 | 0.4921(5) | 0.6964(5) | 0.87895(8) |
| O6 | 0.8051(4) | 0.4132(4) | 1.00436(5) | C23 | 0.6225 | 0.7054 | 0.8832 |
| H6 | 0.7594 | 0.4944 | 1.0130 | C24 | 0.4007(5) | 0.8614(5) | 0.88583(8) |
| H5 | 1.1661(3) | 0.3898(4) | 0.98134(6) | C25 | 1.1696(6) | 0.0555(6) | 0.82565(8) |
| O7 | 0.3932(3) | 0.5920(4) | 0.95236(5) | H25 | 1.1834 | 0.0962 | 0.8436 |
| H7 | 0.3233 | 0.5267 | 0.9607 | C26 | 0.6247(5) | 0.2966(5) | 0.95222(8) |
| O3 | 0.7299(3) | 0.2396(4) | 0.92935(6) | H26A | 0.6419 | 0.2200 | 0.9679 |
| O9 | 0.4874(4) | 0.9925(3) | 0.87524(6) | H26B | 0.4960 | 0.2999 | 0.9476 |
| H9 | 0.4377 | 1.0838 | 0.8800 | C27 | 1.0001(6) | 0.0477(7) | 0.81429(8) |
| O1 | 1.4586(4) | −0.0929(5) | 0.77180(6) | C28 | 1.3185(6) | 0.0050(6) | 0.81125(8) |
| N1 | 0.4163(4) | 0.5547(4) | 0.89343(7) | H28 | 1.4335 | 0.0107 | 0.8194 |
| H1 | 0.3916 | 0.5592 | 0.9108 | C29 | 0.6949(5) | 0.4759(5) | 0.95839(8) |
| O8 | 0.3283(4) | 0.2778(4) | 0.88717(6) | C30 | 0.9999(5) | 0.3486(5) | 0.96800(8) |
| O10 | 0.2645(4) | 0.8741(4) | 0.89885(7) | C31 | 0.9646 | 0.2299 | 0.9732 |
| C11 | 0.4312(6) | 0.4539(6) | 0.84946(8) | H31 | 1.1169 | −0.1207 | 0.7563 |
| H11A | 0.3298 | 0.4241 | 0.8375 | C32 | 1.3007(6) | −0.0541(6) | 0.78493(9) |
| H11B | 0.5382 | 0.3891 | 0.8437 | C33 | 0.6232(6) | 0.7912(6) | 0.96360(10) |
| C12 | 0.9573(5) | 0.5607(6) | 0.85406(8) | H33A | 0.6431 | 0.8133 | 0.9443 |
| H12 | 0.9958 | 0.6661 | 0.8465 | H33B | 0.7354 | 0.8072 | 0.9735 |
| C13 | 0.3865(5) | 0.4168(5) | 0.87861(8) | H33C | 0.5329 | 0.8706 | 0.9705 |
| C14 | 0.8486(5) | 0.3754(5) | 0.92256(8) | C34 | 0.8702(5) | 0.2650(6) | 0.84743(9) |
| C15 | 0.8741(5) | 0.3897(5) | 0.89252(8) | C35 | 1.4493(7) | −0.1195(8) | 0.74303(9) |
| C16 | 1.0276(5) | 0.3544(6) | 0.93752(8) | H35A | 1.3782 | −0.0277 | 0.7345 |
| H16 | 1.1065 | 0.4535 | 0.9330 | H35B | 1.3911 | −0.2303 | 0.7391 |
| O4 | 1.1169(4) | 0.2017(4) | 0.93047(6) | C36 | 0.4675(6) | 0.6470(6) | 0.84892(8) |
| H4 | 1.1707 | 0.2153 | 0.9157 | H36A | 0.3654 | 0.7093 | 0.8408 |
| C18 | 0.8566(5) | 0.4715(6) | 0.97805(7) | H36B | 0.5769 | 0.6728 | 0.8384 |
| H19 | 0.9339(5) | 0.5432(6) | 0.88191(8) | H36 | 0.9832(6) | −0.0189(7) | 0.78851(9) |
| C20 | 0.8467(5) | 0.2519(6) | 0.87543(8) | H37 | 0.8675 | −0.0284 | 0.7807 |
| C38 | 1.6350(7) | −0.1185(9) | 0.73227(10) | H38A | 1.6878 | −0.0052 | 0.7349 |
| H38B | 1.6329 | −0.1455 | 0.7129 | H38C | 1.7066 | −0.2040 | 0.7419 |
| C39 | 0.8361(6) | 0.1133(7) | 0.82948(9) | H39A | 0.7431 | 0.1445 | 0.8161 |
| H39B | 0.7878 | 0.0194 | 0.8407 | O12 | 0.9215(18) | 0.9212(19) | 0.9193(3) |
| H1W | 0.203(9) | 0.807(8) | 0.9582(13) | H2W | 0.112(16) | 0.908(16) | 0.947(2) |

Complex (IA) provided by preparation example 2 and by preparation example 3 have substantially the same X-ray powder diffraction patterns, and substantially the same as the X-ray powder diffraction pattern obtained by simulating in identification example 1. X-Ray powder diffraction pattern of Complex (IA) is shown as FIG. 2, the specific data results are shown as table 4, the peaks position have an error margin of ±0.2°.

TABLE 4

Analysis result of X-ray powder diffraction

| position (°2θ) | d-distance (Å) | relative intensity (%) | position (°2θ) | d-distance (Å) | relative intensity (%) |
|---|---|---|---|---|---|
| 3.6090 | 24.46256 | 99.09 | 7.1384 | 12.37344 | 35.64 |
| 11.4416 | 7.72762 | 39.27 | 11.8418 | 7.46739 | 46.96 |
| 13.3504 | 6.62674 | 62.75 | 16.334 | 5.42225 | 37.61 |
| 16.710 | 5.30125 | 42.61 | 17.1591 | 5.16346 | 64.74 |
| 17.837 | 4.96880 | 14.22 | 18.2150 | 4.86646 | 45.53 |
| 18.515 | 4.78818 | 11.00 | 19.9156 | 4.45458 | 66.49 |
| 21.4292 | 4.14325 | 100.00 | 21.736 | 4.08549 | 12.20 |
| 22.699 | 3.91434 | 52.88 | 22.960 | 3.87039 | 37.49 |
| 23.754 | 3.74280 | 10.48 | 24.313 | 3.65789 | 34.64 |
| 25.067 | 3.54965 | 32.56 | 25.839 | 3.44532 | 30.24 |
| 26.501 | 3.36067 | 9.73 | 27.748 | 3.21243 | 9.48 |
| 28.611 | 3.11742 | 15.20 | 29.246 | 3.05116 | 27.32 |
| 29.436 | 3.03195 | 17.46 | 30.169 | 2.95996 | 10.55 |
| 30.992 | 2.88320 | 9.89 | 31.593 | 2.82965 | 25.96 |
| 32.395 | 2.76145 | 10.08 | 32.808 | 2.72757 | 21.85 |
| 34.315 | 2.61117 | 4.49 | 34.792 | 2.57649 | 10.86 |
| 35.427 | 2.53172 | 10.77 | 36.091 | 2.48667 | 10.71 |
| 38.030 | 2.36421 | 8.41 | | | |

Identification Example 3: Analysis of Differential Scanning Calorimetry (DSC)

A differential scanning calorimetry thermogram was recorded on a TA Instruments™ Q2000 module with a thermoanalysis controller by using a seal disc device. The Complex (IA) sample (about 1 to 5 mg) obtained from preparation example 2 was weighed accurately into a special aluminium crucible with a lid, that is accurate to 0.01 mg, and the sample was transferred to the instrument for measurement. During the test period, DSC cabin was purged with dry nitrogen at a rate of 50 mL/min. The data were collected at a heating rate of 10° C./min from rt to 300° C. Drawing downward with absorption peak, the data were analyzed and showed on TA Instruments Thermal Solutions. The obtained differential scanning calorimetry curve is shown as FIG. 3, which contains an endothermic peak at shift of 96.9° C., there is an error margin of ±3° C. to ±5° C.

Identification Example 4: Analysis of Roman Spectrum

A Roman spectrum was measured on Thermo DXR Laser confocal Raman spectroscopy. Laser wavelength is 780 nm, laser energy is 24 Mw, detection range is from 3500 to 50 $cm^{-1}$, scan times is 20, resolution ratio is from 4.7 to 8.7 $cm^{-1}$. The data were processed and analyzed by using MONIC software. The obtained Raman spectrum of Complex (IA) is shown as FIG. 4, which contains shift at: 1611.92 $cm^{-1}$, 1454.51 $cm^{-1}$, 1303.40 $cm^{-1}$, 1183.17 $cm^{-1}$, 1046.89 $cm^{-1}$, 1012.34 $cm^{-1}$, 875.63 $cm^{-1}$, 844.71 $cm^{-1}$, 819.49 $cm^{-1}$, 692.49 $cm^{-1}$, 495.61 $cm^{-1}$, 371.38 $cm^{-1}$ and 334.03 $cm^{-1}$ characteristic absorption peaks, there is an error margin of ±1 $cm^{-1}$.

Identification Example 5: Analysis Method of Fourier Transform Infrared Spectrum (FT-IR Spectrum)

An infrared spectrum was measured on Bruker TENSOR 27 Fourier transform infrared spectrometer. An appropriate amount of Complex (IA) sample was mixed with dry potassium bromide at ratio of 1:150 by using potassium bromide pellet technique, the mixture was porphyrized and pressed, and the sample was measured at an absorption range of 4000 to 400 $cm^{-1}$. The obtained Fourier transform infrared spectrum of Complex (IA) is shown as FIG. 5, which contains characteristic absorption peaks at: 3648.57 $cm^{-1}$, 3510.87 $cm^{-1}$, 3447.81 $cm^{-1}$, 3259.22 $cm^{-1}$, 2985.55 $cm^{-1}$, 2840.73 $cm^{-1}$, 2725.55 $cm^{-1}$, 2613.90 $cm^{-1}$, 2537.12 $cm^{-1}$, 2378.06 $cm^{-1}$, 1844.06 $cm^{-1}$, 1801.40 $cm^{-1}$, 1750.08 $cm^{-1}$, 1718.01 $cm^{-1}$, 1559.73 $cm^{-1}$, 1550.05 $cm^{-1}$, 1541.26 $cm^{-1}$, 1418.35 $cm^{-1}$, 1410.08 $cm^{-1}$, 1391.46 $cm^{-1}$, 1238.92 $cm^{-1}$, 1222.27 $cm^{-1}$, 1206.04 $cm^{-1}$, 1154.11 $cm^{-1}$, 1124.46 $cm^{-1}$, 1100.65 $cm^{-1}$, 1010.97 $cm^{-1}$, 888.93 $cm^{-1}$, 743.32 $cm^{-1}$, 494.50 $cm^{-1}$ and 446.82 $cm^{-1}$, there is an error margin of +5 $cm^{-1}$ at about 3000 $cm^{-1}$, and an error margin of ±2 $cm^{-1}$ at about 1000 $cm^{-1}$, according to the Chinese Pharmacopoeia.

Identification Example 6: Thermogravimetric Analysis (TGA) Method

The thermogravimetric analysis was carried on a TA Q500 module with a thermoanalysis controller. About 10 mg of Complex (IA) sample (prepared from preparation example 2) was weighed accurately into a platinum sample disc. The data were collected at a heating rate of 10° C./min from rt to 300° C. During the test period, TGA oven chamber was purged with nitrogen at 50 mL/min. The data were processed and analyzed by using TA Instruments Thermal Solutions software.

3. Measurement Examples of Properties

1). Measurement of Solubility

Test method: according to the test method regulated by the Chinese Pharmacopoeia 2010, the micro-powdery test sample (Complex (IA) sample prepared from example 2 of the invention) was weighed and added into a certain amount of solvent, then the mixture was shook vigorously for 30 sec every other 5 min, and the solubility was observed in 30 min, which was dissolved completely if there was no visible solute particle or liquid drop.

Judgement standard of solubility are shown as table A.

TABLE A

| | |
|---|---|
| Very soluble | 1 g (mL) of solute can be dissolved completely in a <1 mL of solvent |
| Freely soluble | 1 g (mL) of solute can be dissolved completely in a 1 to <10 mL of solvent |
| Soluble | 1 g (mL) of solute can be dissolved completely in a 10 to <30 mL of solvent |
| Sparingly Soluble | 1 g (mL) of solute can be dissolved completely in a 30 to <100 mL of solvent |
| Slightly Soluble | 1 g (mL) of solute can be dissolved completely in a 100 to <1000 mL of solvent |
| Very Slightly Soluble | 1 g (mL) of solute can be dissolved completely in a 1000 to <10 000 mL of solvent |
| Practically Insoluble | 1 g (mL) of solute can not be dissolved completely in a 10 000 mL of solvent |

The solubility was recorded, and the specific was listed in table 5.

TABLE 5

Test results of solubility of Complex (IA)

| test number | sampling weight | solvent | solvent volume (mL) | yes/no dissolved | results |
|---|---|---|---|---|---|
| 1 | 100.20 | acetonitrile | 2.90 | yes | Soluble |
| 2 | 100.23 | methanol | 0.095 | yes | Very soluble |
| 3 | 100.16 | DMSO | 0.095 | yes | Very soluble |
| 4 | 100.02 | DMA | 0.095 | yes | Very soluble |
| 5 | 10.33 | water | 102 | no | Practically Insoluble |
| 6 | 100.10 | ethanol | 2.90 | yes | Soluble |

Test results: From the data analysis listed in table 5, Complex (IA) has a good solubility in acetonitrile, methanol, ethanol, DMSO and DMA.

2). Measurement of Stability

An appropriate amount of the Complex (IA) sample (prepared from example 2) was weighed and tiled on a clean culture dish at a thickness of ≤5 mm, and analyzed under the following conditions:

2.1) High-Temperature Test

The test sample was placed under a high temperature condition (60±2° C.) for 10 d, the relative indexes were measured at the fifth and tenth days. If the test sample had changed significantly, the test was carried out at 40° C. using the same method. If no significant change, the test at 40° C. was not necessary.

2.2) High-Humidity Test

The test sample was placed under a 25° C. and RH 90%±5% condition for 10 d, and the sample were measured at the fifth and tenth days. Test items should include a moisture-absorption weight gain. If weighting percentage of moisture absorption was more than 5%, the test should be carried out under a 25° C. and RH 75%±5% condition using the same method; If weighting percentage of moisture absorption was less than 5%, and other inspection items met the requirements, the test was not necessary. The constant humidity condition can be realized by adopting constant temperature humidity chamber or placing a saturated saline solution under a closed container. According to a variety of demand of humidity, a saturated aqueous NaCl solution (15.5-60° C., RH75%±14%) or a saturated aqueous $KNO_3$ solution (25° C., RH 92.5%) was selected.

2.3) Photostability Test

The test sample was placed in light box or other suitable light vessel under a 4500 Lx±500 Lx of illuminance condition for 10 d, and the sample were measured at the fifth and tenth days.

The impurity content of the sample was calculated by the normalization method of peak area using an HPLC chromatographic instrument under the above condition, the analytic conditions were shown below:

The detection was performed on Agilent 1200DAD high pressure liquid chromatography spectrometer (Zorbax Eclipse Plus C18 150×4.6 mm chromatographic column).

The test condition of HPLC: the run time was 30 minutes (min); the column temperature was 35° C.; the detection was carried out at the wavelength of 210 nm and 225 nm;

Mobile phase: phase C: acetonitrile phase D: ultrapure water flow rate: 1.0 mL/min.

Gradient elution, the ratio of mobile phase was shown as table B.

TABLE B

| Time | gradient condition of phase C | gradient condition of phase D |
|---|---|---|
| 0 min | 20% | 80% |
| 4.0 min | 37% | 63% |
| 12 min | 50% | 50% |
| 20 min | 90% | 10% |
| 30 min | 90% | 10% |

The test results of stability of Complex (IA) were shown as table 6.

TABLE 6

The results of content determination of Complex (IA) under a accelerated condition

| test sample | item | condition 0 d | high-temperature 5 d | high-temperature 10 d | high humidity 5 d | high humidity 10 d | illumination 5 d | illumination 10 d |
|---|---|---|---|---|---|---|---|---|
| compound (I-n) amorphism | appearance | white powder | transparent bulk | transparent bulk | white bulk | white bulk | white bulk | white bulk |
| | total impurity (%) | 0.25 | 4.97 | 7.84 | 0.30 | 0.22 | 0.31 | 0.28 |
| | purity (%) | 99.75 | 95.03 | 92.16 | 99.70 | 99.78 | 99.69 | 99.72 |
| Complex (IA) | appearance | white powder | white powder | white powder | white powder | white powder | white powder | white powder |
| | total impurity (%) | 0.15 | 0.17 | 0.19 | 0.15 | 0.19 | 0.17 | 0.22 |
| | purity (%) | 99.85 | 99.83 | 99.81 | 99.85 | 99.81 | 99.83 | 99.78 |

Test results: the purity results at a detection wavelength of 210 nm showed that the appearance of compound (I-n) in amorphism form had changed under a condition of high-temperature, high humidity or illumination for 10 d, especially under a condition of high temperature, the impurity was increased significantly, which has a poor stability. And the appearance of Complex (IA) did not change, and the purity almost had no change, and no obvious new impurity occurred, which have a good stability and meet the drug demand.

3). Measurement of Hygroscopicity

Test method: According to the method regulated by Chinese pharmacopoeia 2010, part II, appendix XIXJ, a dry glass weighing bottle with a stopper (outside diameter is 50 mm, high is 15 mm) was placed in a thermostatic drier (an ammonium chloride or ammonium sulfate saturated solution was placed in the bottom) at 25° C.±1° C. before one day of experiment, the empty glass weighing bottle with a stopper was weighed accurately by using METTLERTOLEDO XP205DR analytical balance, and recorded as $m_1$. An appropriate amount of the Complex (IA) sample (prepared from example 2) was tiled on the above weighing bottle at a thickness of 1 mm, which was weighed accurately and recorded as $m_2$. Opening the bottle, the bottle was placed under the above constant temperature and humidity condition for 24 h with the stopper. Closing the bottle with the stopper, the bottle was weighed accurately, and recorded as $m_3$, the weight gain percentage (%) was calculated.

$$\text{weight gain percentage (\%)} = \frac{m_3 - m_2}{m_2 - m_1} \times 100\%$$

The judgement of the results hygroscopicity was shown as table C.

TABLE C

| hygroscopicity characteristics | weighting percentage of moisture absorption |
|---|---|
| deliquescence | absorbing enough water and forming liquid |
| very hygroscopicity | weighting percentage of moisture absorption is no less than 15% |
| hygroscopicity | weighting percentage of moisture absorption is less than 15%, and no less than 2% |
| Sparingly hygroscopicity | weighting percentage of moisture absorption is less than 2%, and no less than 0.2% |
| No or almost no hygroscopicity | weighting percentage of moisture absorption is less than 0.2% |

The hygroscopicity results of Complex (IA) were shown as table 7.

TABLE 7

The hygroscopicity results of Complex (IA)

| test sample | $m_1$ (g) | $m_2$ (g) | $m_3$ (g) | weight gain percentage (%) | results |
|---|---|---|---|---|---|
| Complex (IA) | 29.29037 | 30.29260 | 30.29542 | 0.27 | Sparingly hygroscopicity |

Test results: table 7 results showed that, Complex (IA) had a little weight gain under the high humidity environment, and had sparingly hygroscopicity.

4. Pharmacokinetic Evaluation after Administration of the Quantitative Complex (IA) by Intravenous Injection and Oral 1) Test Method of Pharmacokinetic Evaluation in Rats The test sample (Complex (IA) prepared from example 2 of the invention) was dissolved in normal saline (100%) to get a solution at a concentration of 0.06 mg/mL, which was administered by i.v; the same test sample was suspended in 0.5% HPMC to get a suspension at a concentration of 0.03 mg/mL, 0.15 mg/mL, 0.75 mg/mL, which was administered by gavage. The rats were grouped randomly, each dosage group has 6 rats, half male and half female, which were fasted for 12 h before administered, free drank. After administration of 4 h, rats uniform ate. A single gastric administration was adopted in oral administration. The gavage group was grouped to 3 dosage groups, which were administered the test sample suspension by gavage respectively, the dosage respectively was 0.3, 1.5 and 7.5 mg/kg, the volume of the suspension was 10 mL/kg. The blood samples were collected before administration of 0 h, and after administration of 0.25, 0.5, 1.0, 2.0, 4.0, 6.0, 8.0, 10, 12 and 24 h from caudal vein, which were placed into EDTA-$K_2$ anticoagulative tubes. The i.v group had one dosage group, the test sample solution was administered by i.v at a dosage of 0.3 mg/kg, and the volume of the solution was 5 mL/kg. The blood samples were collected before administration of 0 h, and after administration of 5 min, 15 min, 0.5, 1.0, 2.0, 4.0, 6.0, 8.0, 10, 12 and 24 h from vein, which were placed into EDTA-$K_2$ anticoagulative tubes. The blood samples were centrifuged for 2 min at 11000 rpm, the plasma samples were isolated and stored at −70±10° C.

2) Test Method of Pharmacokinetic Evaluation in Beagles

The test sample (Complex (IA) prepared from example 2 of the invention) was dissolved in normal saline (100%) to get a solution at a concentration of 0.04 mg/mL, which was administered by i.v; the same test sample was suspended in 0.5% HPMC to get a suspension at a concentration of 0.02 mg/mL, 0.10 mg/mL, 0.50 mg/mL, 2.00 mg/mL, which was administered by gavage. The beagles were grouped randomly, each dosage group had 6 beagles, half male and half female, which were fasted for 12 h before administered, free drank. After administration of 4 h, beagles uniform ate. The single oral administration group was grouped to 4 dosage groups, which were administered the test sample suspension by gavage respectively, the dosage respectively was 0.1, 0.5, 2.5 and 10 mg/kg, and the volume of the suspension was 5 mL/kg. The blood samples were collected before administration of 0 h, and after administration of 0.25, 0.5, 1.0, 2.0, 4.0, 6.0, 8.0, 10, 12 and 48 h from lateral small saphenous vein or medial head vein of forelimb, which were placed into EDTA-$K_2$ anticoagulative tubes. The i.v group had one dosage group, the test sample solution was administered by i.v at a dosage of 0.1 mg/kg, and the volume of the solution was 2.5 mL/kg. The blood samples were collected before administration of 0 h, and after administration of 5 min, 15 min, 0.5, 1.0, 2.0, 4.0, 6.0, 8.0, 10, 12 and 48 h from lateral small saphenous vein or medial head vein of forelimb, which were placed into EDTA-$K_2$ anticoagulative tubes. The blood samples were centrifuged for 2 min at 11000 rpm, the plasma samples were isolated and stored at −70° C.±10° C.

3) Analysis Method of the Sample

The concentration of the test sample in plasma was analyzed by the LC-MS/MS method, the pharmacokinetic parameters were calculaged by the non atrioventricular model method using WinNonlin 6.3 software, and drug-time curve was plotted.

The LC/MS/MS system comprised Agilent 1200 series vacuum degassing furnace, binary pumps, well-plate autosampler, thermostatted column compartment, the API 4000 QTRAP Triple Quadrupole Mass Spectrometer with an electrosprayionization (ESI) source. Quantitative analysis was carried out using MRM mode. Each parameters was listed in Table D.

TABLE D

| Ion source | ESI |
|---|---|
| Multiple Reaction Monitoring | 449.1→302.9 |
| IS | −4500 V |
| Curtain GS | 0.18 MPa |

TABLE D-continued

| Ion source | ESI |
|---|---|
| GS1 | 0.49 MPa |
| GS2 | 0.49 MPa |
| temperature | 600° C. |

A Waters Xbridge-C18, 2.1×30 mm, 3.5 μM column was used for the analysis, 5 μL of the sample was injected. Analysis condition: The mobile phase was 2 nM ammonium formate+0.1% formic acid in water (A) and 2 mM ammonium formate+0.1% formic acidin methanol (B). The flow rate was 0.4 mL/min And the gradient of Mobile phase was in the Table E.

TABLE E

| Time | Gradient of Mobile Phase B |
|---|---|
| 0.0 min | 30% |
| 1.0 min | 30% |
| 1.5 min | 95% |
| 3.8 min | 95% |
| 3.9 min | 30% |
| 5.0 min | 30% |

The test results of pharmacokinetic characteristics of Complex (IA) were shown as table 8.

TABLE 8

The test results of pharmacokinetic characteristics of Complex (IA) in beagles

| test sample | drug delivery route | dosage (mg/kg) | $T_{1/2}$ (h) | $C_{max}$ (ng/mL) | $AUC_{last}$ (ng · h/mL) | F (%) |
|---|---|---|---|---|---|---|
| Complex (IA) | i.v | 0.1 | 8.97 | 148 | 617 | N/A |
| | p.o | 0.1 | 8.88 | 66.2 | 602 | 97.57 |

Test results: Complex (IA) had good pharmacokinetic properties when administered by i.v or oral, and the absorption was good, the exposure was high, the oral bioavailability (F) was very high, and it also had a long half-life ($T_{1/2}$). Specifically, Complex (IA) had a high exposure ($AUC_{last}$) in beagle, which showed that Complex (IA) was absorbed easily and had a better stability; the absolute bioavailability reaches 97.5% in beagle, which shows that Complex (IA) has a super high bioavailability; the half-life reached 8.88 h, which showed that Complex (IA) has a lasting efficacy, and the dosage interval can be extended appropriately, the times of administration can be decreased.

5. Detection of Inhibitory Activity Against SGLT-2 and SGLT-1

Test Purpose:
The following method was used for detecting inhibitory activity of the compounds of the invention against SGLT-1 and SGLT-2.

Experimental Materials:
[14]C-AMG solution purchased from PerkinElmer, Cat. No. NEZ080001MC;
α-Methyl Glucopyranoside purchased from Sigma, Cat. No. M9376-100G;
Meglumine purchased from Sigma, Cat. No. M2004-100G;
Phlorhizin purchased from Sigma, Cat. No. P3449-1G;
96-well cell culture plate purchased from Corning, Cat. No. 3903.

Test Method:
$3 \times 10^4$ of FIP-in CHO cells transfected Mock and CHO cells expressing human SGLT-1/SGLT-2 gene were seeded into a 96-well cell culture plate; the cells were incubated for 12 hours, and then to each well was added 150 μL of Na-free buffer to wash the cells once; and then to each well were added 50 μL of Na buffer containing the compound at different concentrations and 0.5 μM [$^{14}$C]-AMG, and the plate was incubated in a incubator at 37° C. for 1 hour, the reaction was terminated by adding 150 μL of pre-cooled Na-free buffer; the cells were further washed with Na-free buffer 3 times and the residual liquid was removed; to each well was added 20 μL of pre-cooled NaOH (100 nM), the plate was vibrated at 900 rpm for 5 min; and then to each well was added 80 μL of scintillation solution, the plate was vibrated at 600 rpm for 5 min; the plate was analyzed on liquid scintillation counter.

The experimental results show that the complex disclosed herein has SGLT-2 and SGLT-1 inhibitory activity, and the inhibitory activity to SGLT-2 is much more stronger than that to SGLT-1.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure. All publications or patents cited herein are incorporated by reference herein.

What is claimed is:

1. A complex having Formula (IA):

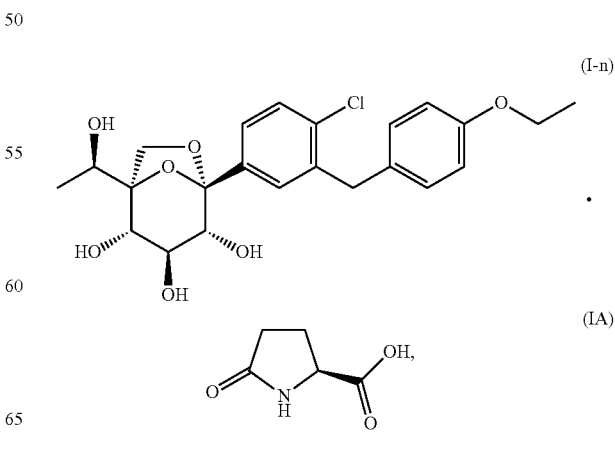

or a hydrate thereof, wherein the complex comprises a compound having Formula (I-n) and L-pyroglutamic acid at a mole ratio of 1:1,

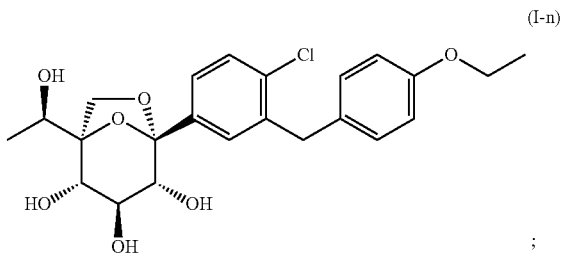 [SMILES: CCOc1ccc(Cc2cc([C@]34OC[C@]([C@@H](C)O)(O3)[C@@H](O)[C@H](O)[C@H]4O)ccc2Cl)cc1]

Figure 2:
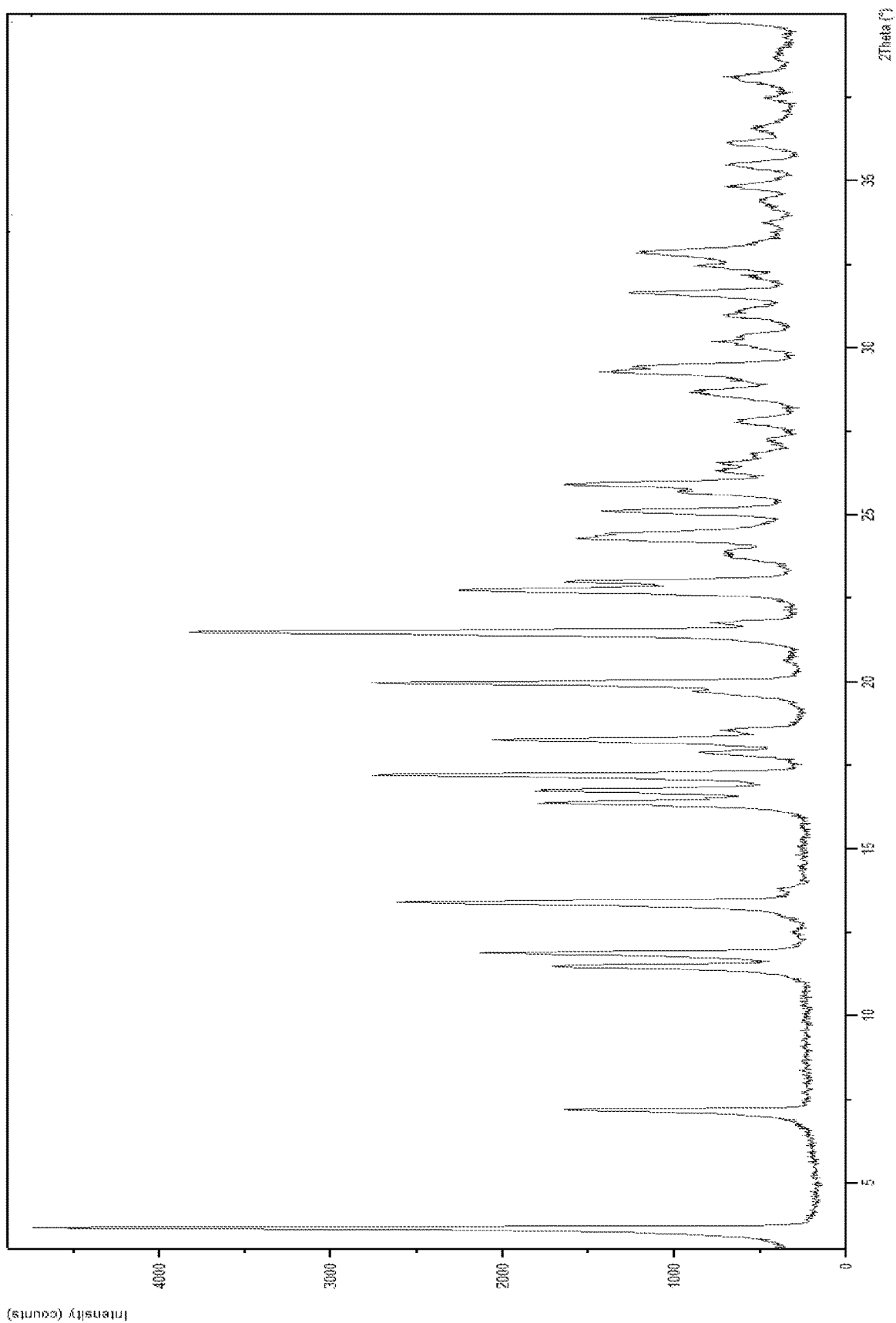
FIG. 2 is the X-ray powder diffraction (XRPD) pattern of Complex (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid prepared herein.

(I-n)

wherein the complex is in a crystalline form, and wherein the crystalline form has an X-ray powder diffraction pattern:
comprising peaks at scattering angles (2θ) of 3.61°±0.2°, 13.35°±0.2°, 17.84°±0.2°, 18.22°±0.2°, 19.92°±0.2° and 21.43°±0.2°; or
comprising peaks at scattering angles (2θ) of 3.61°±0.2°, 7.14°±0.2°, 13.35°±0.2°, 17.84°±0.2°, 18.22°±0.2°, 19.92°±0.2°, 21.43°±0.2° and 22.70°±0.2°; or
comprising peaks at scattering angles (2θ) of 3.61°±0.2°, 7.14°±0.2°, 11.44°±0.2°, 11.84°±0.2°, 13.35°±0.2°, 16.33°±0.2°, 16.71°±0.2°, 17.16°±0.2°, 17.84°±0.2°, 18.22°±0.2°, 19.92°±0.2°, 21.43°±0.2°, 22.70°±0.2° and 22.96°±0.2°; or
comprising peaks at scattering angles (2θ) of 3.61°±0.2°, 7.14°±0.2°, 11.44°±0.2°, 11.84°±0.2°, 13.35°±0.2°, 16.33°±0.2°, 16.71°±0.2°, 17.16°±0.2°, 17.84°±0.2°, 18.22°±0.2°, 18.52°±0.2°, 19.92°±0.2°, 21.43°±0.2°, 21.74°±0.2°, 22.70°±0.2°, 22.96°±0.2°, 23.75°±0.2°, 24.31°±0.2°, 25.07°±0.2°, 25.84°±0.2°, 26.50°±0.2°, 27.75°±0.2°, 28.61°±0.2°, 29.25°±0.2°, 29.44°±0.2°, 30.17°±0.2°, 30.99°±0.2°, 31.59°±0.2°, 32.40°±0.2°, 32.81°±0.2°, 34.32°±0.2°, 34.79°±0.2°, 35.43°±0.2°, 36.09°±0.2° and 38.03°±0.2°; or
substantially the same as shown in FIG. 2.

2. The complex of claim 1, wherein the complex is a hydrate containing 1.25 equivalents of water of crystallization.

3. The complex of claim 1, wherein the crystalline form has at least one of the following features:
(i) a differential scanning calorimetry thermogram comprising an endothermic peak at 96.9° C.±3° C.;
(ii) a Raman spectrogram comprising absorption peaks at 1454.51 cm$^{-1}$±1 cm$^{-1}$, 1303.40 cm$^{-1}$±1 cm$^{-1}$, 1183.17 cm$^{-1}$±1 cm$^{-1}$, 1012.34 cm$^{-1}$±1 cm$^{-1}$ and 495.61 cm$^{-1}$±1 cm$^{-1}$; and
(iii) a Fourier transform infrared spectrogram comprising absorption peaks at 3259.22 cm$^{-1}$±5 cm$^{-1}$, 2985.55 cm$^{-1}$±5 cm$^{-1}$, 2926.65 cm$^{-1}$±5 cm$^{-1}$, 1750.08 cm$^{-1}$±2 cm$^{-1}$, 1648.90 cm$^{-1}$±2 cm$^{-1}$, 1511.90 cm$^{-1}$±2 cm$^{-1}$, 1475.81 cm$^{-1}$±2 cm$^{-1}$, 1263.43 cm$^{-1}$±2 cm$^{-1}$, 1238.92 cm$^{-1}$±2 cm$^{-1}$, 1206.04 cm$^{-1}$±2 cm$^{-1}$, 1088.08 cm$^{-1}$±2 cm$^{-1}$, 1060.72 cm$^{-1}$±2 cm$^{-1}$, 1010.97 cm$^{-1}$±2 cm$^{-1}$ and 821.26 cm$^{-1}$±2 cm$^{-1}$.

Figure 3:
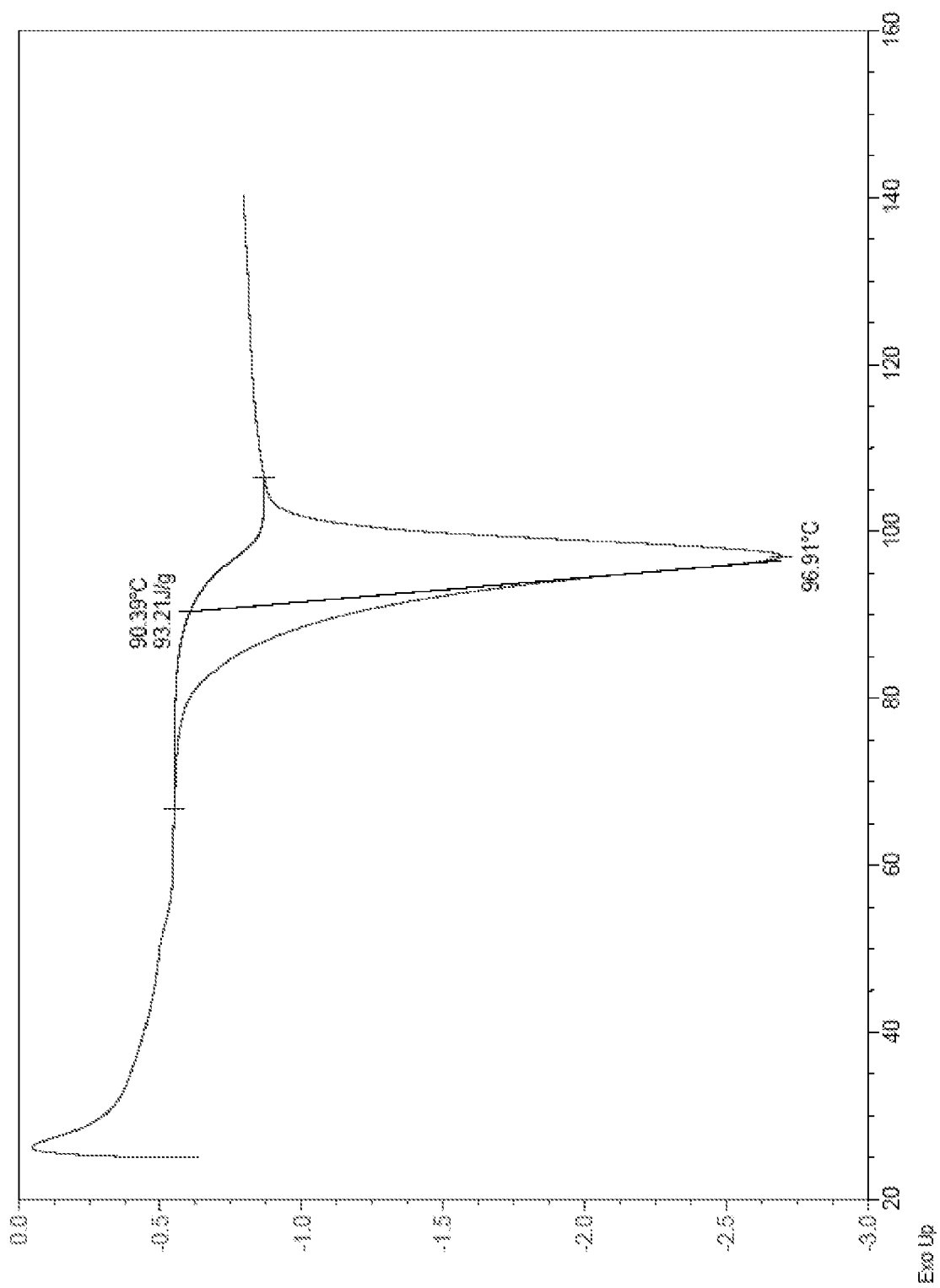
FIG. 3 is the differential scanning calorimetry (DSC) curve of Complex (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid prepared herein.
Figure 4:
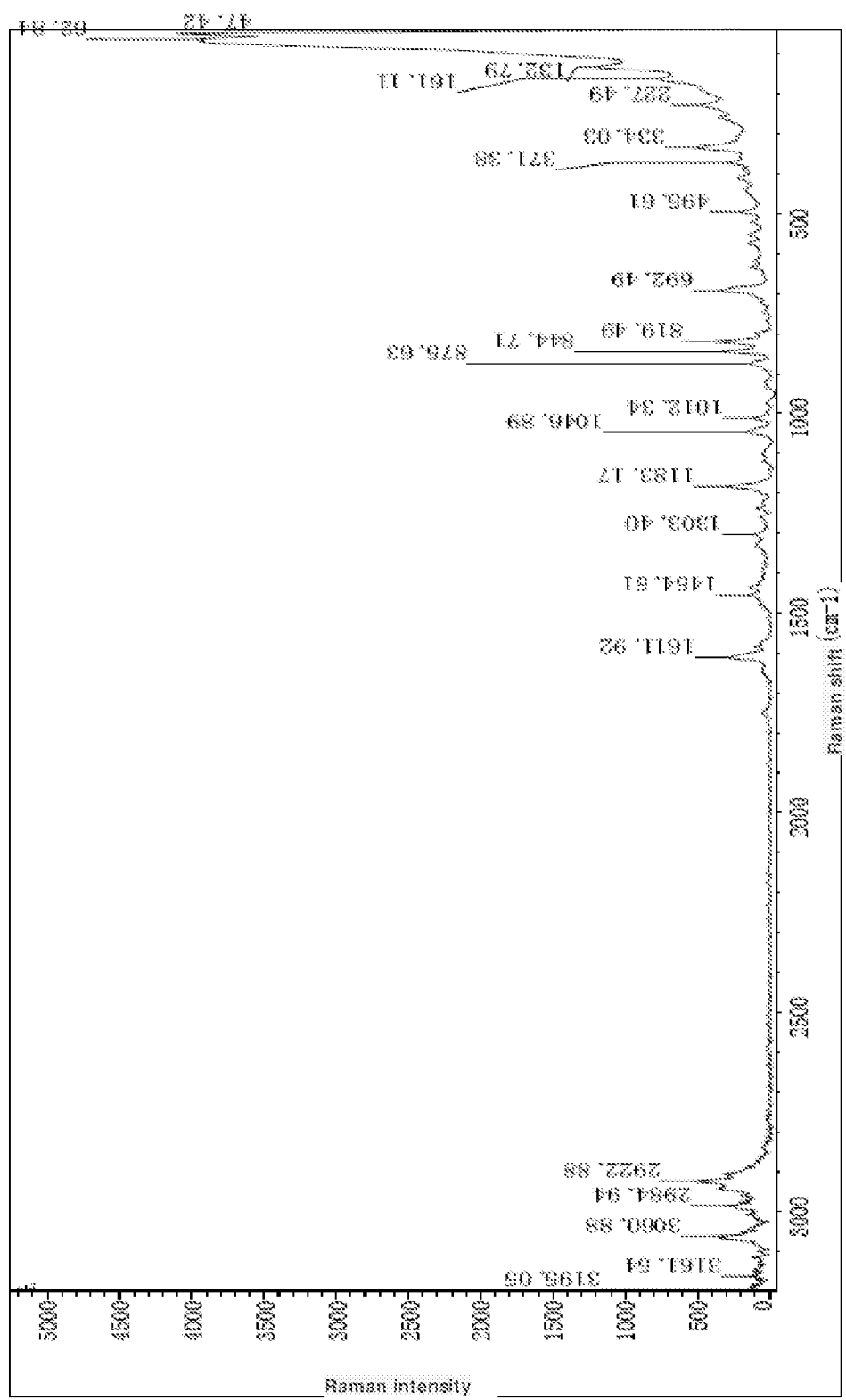
FIG. 4 is the Raman spectrum of Complex (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid prepared herein.
Figure 5:
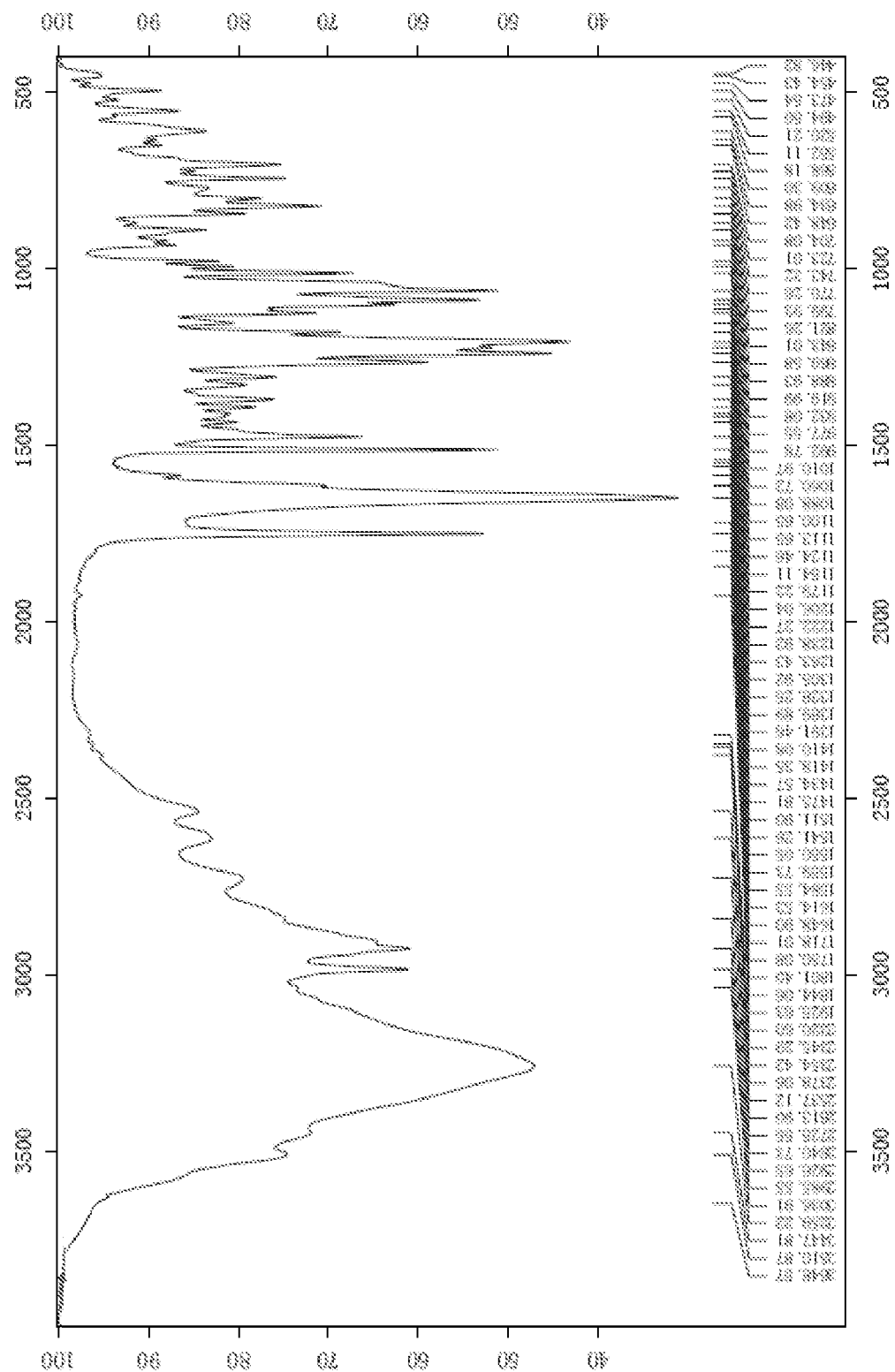
FIG. 5 is the FT-IR spectrum of Complex (IA) of (1R,2S,3S,4R,5S)-5-(4-chloro-3-(4-ethoxybenzyl)phenyl)-1-((1R)-1-hydroxyethyl)-6,8-dioxabicyclo[3.2.1]octane-2,3,4-triol (I-n) and L-pyroglutamic acid prepared herein.

4. The complex of claim 1, wherein the crystalline form has at least one of the following features:
(i) a differential scanning calorimetry thermogram substantially the same as shown in FIG. 3;
(ii) a Raman spectrogram substantially the same as shown in FIG. 4;
(iii) a Fourier transform infrared spectrogram substantially the same as shown in FIG. 5; and (iv) the following unit cell parameters:
unit cell dimension: a=7.4751 (2) Å, b=7.8333 (3) Å, c=49.4417 (19) Å, α=90°, β=90°, γ=90°;
space group: orthogonality, P 2$_1$ 2$_1$ 2$_1$;
cell volume: 2895.04 Å$^3$; and
number of asymmetric units per unit cell (Z): 4.

5. A pharmaceutical composition comprising the complex of claim 1, optionally, further comprising a pharmaceutically acceptable adjuvant.

6. The pharmaceutical composition of claim 5 further comprising an additional therapeutic agent, wherein the additional therapeutic agent is an anti-diabetic agent other than an SGLT-2 inhibitor, an antihyperglycemic agent, an antiadipositas drug, an antihypertensive agent, an antiplatelet agent, an antiatheroaclerotic drug, a lipid-lowering agent, an anti-inflammatory or a combination thereof.

7. The pharmaceutical composition of claim 6, wherein the anti-diabetic agent other than an SGLT-2 inhibitor is a biguanide, a sulfonylurea, a glucosidase inhibitor, a PPAR agonist, an αP2 inhibitor, a PPARα/γ dual agonist, a dipeptidyl peptidase IV inhibitor, a glinide, insulin, a glucagon-like peptide-1 inhibitor, a PTP1B inhibitor, a glycogen phosphorylase inhibitor, a glucose-6-phosphatase inhibitor or a combination thereof;
wherein the antihyperglycemic agent is a biguanide, a sulfonylurea, a glucosidase inhibitor, a PPAR agonist, an αP2 inhibitor, a PPARα/γ dual agonist, a dipeptidyl peptidase IV inhibitor, a glinide, insulin, a glucagon-like peptide-1 inhibitor, a PTP1B inhibitor, a glycogen phosphorylase inhibitor, a glucose-6-phosphatase inhibitor or a combination thereof;
wherein the lipid-lowering agent is an MTP inhibitor, an HMGCoA reductase inhibitor, a squalene synthase inhibitor, a fibrate antihyperlipidemic drug, an ACAT inhibitor, a lipoxygenase inhibitor, a cholesterol absorption inhibitor, an ileal Na(+)/bile acid cotransporter inhibitor, an upregulator of LDL receptor activity, a nicotinic antihyperlipidemic drug, a bile acid sequestrant or a combination thereof; or
the lipid-lowering agent is pravastatin, simvastatin, atorvastatin, fluvastatin, cerivastatin, atavastatin, rosuvastatin or a combination thereof.

8. A process of preparing the complex of claim 1, wherein the process comprises the steps of:
(i) dissolving the compound having Formula (I-n) and L-pyroglutamic acid in a solvent;
(ii) cooling the solution obtained from step (i) to precipitate a solid; and
(iii) separating the solid obtained from step (ii).

9. The process of claim 8, in step (i), wherein the solvent is a mixture of ethanol and water at a volume ratio from (1:1) to (1:2) or a mixture of isopropanol and water at a volume ratio from (1:1) to (1:2).

10. The process of claim 8, in step (i), wherein the amount of the solvent is from 1.5 mL to 5 mL per gram of the compound having Formula (I-n).

11. The process of claim 8, wherein the mole ratio of the compound having Formula (I-n) and L-pyroglutamic acid in step (i) is from (1:2) to (1:5) or from (1:3) to (1:4).

12. The process of claim 8, wherein the dissolving temperature in step (i) is from 70° C. to 90° C.

13. The process of claim 8, wherein the cooling in step (ii) is natural cooling at a temperature from 10° C. to 30° C.

14. The process of claim 8, wherein the separating in step (iii) is filtration under vacuum suction, wherein the filtration under vacuum suction further comprises washing the solid after separation, wherein the solid after separation is washed with a mixture of ethanol and water at a volume ratio from (1:1) to (1:2) or a mixture of isopropanol and water at a volume ratio from (1:1) to (1:2), and wherein the mixture is pre-cooled to a temperature from 20° C. to 0° C.

15. A process of preparing the complex of claim 1, wherein the process comprises the steps of:
(i) dissolving the compound having Formula (I-n) and L-pyroglutamic acid in a solvent;
(ii) cooling the solution obtained from step (i) to precipitate a solid; and
(iii) separating the solid obtained from step (ii),
wherein,
in step (i),
the solvent is a mixture of ethanol and water at a volume ratio (1:1) to (1:2) or a mixture of isopropanol and water at a volume ratio from (1:1) to (1:2);
the amount of the solvent is from 1.5 mL to 5 mL per gram of the compound having Formula I-n,
the mole ratio of the compound having Formula (I-n) and L-pyroglutamic acid is from (1:3) to (1:4), and
the dissolving temperature is from 70° C. to 90° C.,
in step (ii),
the cooling is natural cooling at a temperature from 10° C. to 30° C.,
in step (iii),
the separating is filtration under vacuum suction, wherein the filtration under vacuum suction further comprises washing the solid after separation, wherein the solid after separation is washed with a mixture of ethanol and water at a volume ratio from (1:1) to (1:2) or a mixture of isopropanol and water at a volume ratio from (1:1) to (1:2), and wherein the mixture is precooled to a temperature from −20° C. to 0° C.

16. A method of inhibiting SGLT-2, inhibiting SGLT-1, elevating the high density lipoprotein level, treating, lessening or delaying a disease in a patient comprising administering a therapeutically effective amount of the complex of claim 1 to the patient, wherein the disease is diabetes, a diabetic complication, insulin resistance, hyperglycemia, hyperinsulinemia, elevated blood levels of fatty acids or glycerol, hyperlipidemia, obesity, syndrome X, atherosclerosis or hypertension,
wherein diabetic complication comprises at least of one of diabetic retinopathy, diabetic neuropathy, and diabetic nephropathy;
wherein hyperlipidemia comprises hypertriglyceridemia.

17. A method of inhibiting SGLT-2, inhibiting SGLT-1, elevating the high density lipoprotein level, treating, lessening or delaying a disease in a patient comprising administering a therapeutically effective amount of the pharmaceutical composition of claim 5 to the patient, wherein the disease is diabetes, a diabetic complication, insulin resistance, hyperglycemia, hyperinsulinemia, elevated blood levels of fatty acids or glycerol, hyperlipidemia, obesity, syndrome X, atherosclerosis or hypertension,
wherein diabetic complication comprises at/at least of one of diabetic retinopathy, diabetic neuropathy, and diabetic nephropathy;
wherein hyperlipidemia comprises hypertriglyceridemia.

* * * * *